United States Patent
Helgeson et al.

(10) Patent No.: US 8,043,263 B2
(45) Date of Patent: *Oct. 25, 2011

(54) SLITTABLE DELIVERY DEVICE ASSEMBLY FOR THE DELIVERY OF A CARDIAC SURGICAL DEVICE

(75) Inventors: Heather Helgeson, Hudson, WI (US); Dale Price, Coon Rapids, MN (US); John Hastings, Savage, MN (US); Brian Swanson, St. Paul, MN (US); Ross Marks, Raleigh, NC (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/411,274

(22) Filed: Mar. 25, 2009

(65) Prior Publication Data

US 2010/0094226 A1 Apr. 15, 2010

Related U.S. Application Data

(63) Continuation-in-part of application No. 12/248,802, filed on Oct. 9, 2008, now Pat. No. 7,824,375.

(51) Int. Cl.
*A61M 5/178* (2006.01)
(52) U.S. Cl. ........................ 604/160; 604/161
(58) Field of Classification Search .................. 604/160, 604/161, 163
See application file for complete search history.

(56) References Cited

U.S. PATENT DOCUMENTS

| | | | |
|---|---|---|---|
| 4,354,491 A * | 10/1982 | Marbry | 604/160 |
| 4,402,685 A | 9/1983 | Buhler et al. | |
| 4,921,479 A | 5/1990 | Grayzel | |
| 4,997,424 A | 3/1991 | Little | |
| 5,188,605 A | 2/1993 | Sleep | |
| 5,221,263 A | 6/1993 | Sinko et al. | |
| 5,312,355 A | 5/1994 | Lee | |
| 5,755,693 A * | 5/1998 | Walker et al. | 604/160 |
| 6,083,207 A | 7/2000 | Heck | |
| 6,159,198 A | 12/2000 | Gardeski et al. | |
| 6,497,681 B1 | 12/2002 | Brenner | |
| 6,623,460 B1 * | 9/2003 | Heck | 604/256 |
| 6,712,791 B2 | 3/2004 | Lui et al. | |
| 6,966,896 B2 | 11/2005 | Kurth et al. | |
| 2003/0050604 A1 | 3/2003 | Lui et al. | |
| 2004/0054330 A1 | 3/2004 | Kurth et al. | |
| 2004/0267202 A1 * | 12/2004 | Potter | 604/158 |
| 2005/0267487 A1 * | 12/2005 | Christensen et al. | 606/108 |
| 2006/0052749 A1 * | 3/2006 | Moyer | 604/160 |
| 2009/0018508 A1 * | 1/2009 | Fisher et al. | 604/167.04 |

OTHER PUBLICATIONS

NonFinal Office Action, mailed Dec. 11, 2009—U.S. Appl. No. 12/248,802.

(Continued)

*Primary Examiner* — Nicholas D Lucchesi
*Assistant Examiner* — Gerald Landry, II

(57) ABSTRACT

An assembly for the delivery of a cardiac surgical device is disclosed herein. In one embodiment, the assembly includes a slittable delivery device and a bypass assembly. The slittable delivery device may include a hub, a shaft integrated into the hub and forming at least a segment of the circumferential surface of the hub, and a hemostasis valve contained substantially within the hub. The bypass assembly may include a cap and a valve bypass tool. The cap may be on a proximal end of the hub and may include an opening in the cap extending radially outward from a point near a radial center of the cap through a circumferential edge of the cap. The valve bypass tool may be operably coupled to the cap and may include a longitudinally extending open channel.

24 Claims, 34 Drawing Sheets

OTHER PUBLICATIONS

Final Office Action, mailed May 13, 2010—U.S. Appl. No. 12/248,802.

Notice of Allowance, mailed Sep. 1, 2010—U.S. Appl. No. 12/248,802.

* cited by examiner

SLITTABLE DELIVERY DEVICE ASSEMBLY FOR THE DELIVERY OF A CARDIAC SURGICAL DEVICE

CROSS REFERENCE TO RELATED APPLICATIONS

This application is a continuation-in-part ("CIP") of U.S. application Ser. No. 12/248,802, filed Oct. 9, 2008, entitled "Slittable Delivery Device for the Delivery of a Cardiac Surgical Device," and is incorporated by reference herein in its entirety.

FIELD OF THE INVENTION

The present invention relates to medical apparatus and methods. More specifically, the present invention relates to delivery device assemblies for cardiac surgical devices, such as implantable cardiac electrotherapy leads, guidewires, inner catheters, outer sheaths, and other accessories, methods of manufacturing such delivery device assemblies and kits including the same.

BACKGROUND OF THE INVENTION

Implantable pulse generators, such as pacemakers, defibrillators or implantable cardioverter defibrillators ("ICD") provide electrotherapy to cardiac tissue via implantable cardiac electrotherapy leads. Delivery devices, such as delivery catheters or sheaths, are used to place leads in specific cardiac anatomies during implantation of the pulse generator. The delivery devices also navigate the venous system and cardiac anatomy to locate specific anatomical locations and serve as a conduit through which leads and other cardiac surgical devices are delivered. Upon placement of the lead, the delivery catheter is removed and care is taken to not disrupt the position of the implanted lead. Non-disruptive removal is also advantageous when the delivery devices are used to deliver other cardiac surgical devices, such as inner catheters, outer sheaths, guidewires and other accessories.

A common technique for accomplishing the non-disruptive removal of the delivery device involves slitting or otherwise cutting the catheter over the lead or other cardiac surgical device using a small blade known as a slitter. A typical catheter used in this technique is designed such that the force required to slit the sheath is as low and as consistent as possible. However, the hub of the delivery catheter typically requires considerably more force to slit through than is required for the shaft. That is, when slitting the catheter, the user begins by generating enough force to slit through the hub. As the slitter transitions from the hub to shaft, this force is excessively high and results in an acceleration or jerk. In the context of an implantable cardiac lead, if this jerk is severe, it may tear the cardiac tissue or disrupt lead placement, which results in a major procedural delay. Similarly, disruption of other cardiac surgical tools, such as an inner catheter, may cause damage to cardiac tissue or major procedural delays.

In order to prevent vascular bleedback, delivery devices may have a hemostasis valve coupled thereto to provide hemostasis sealing around the cardiac surgical devices. Leads or other devices to be passed through the hemostasis valve are often soft and flimsy. As a result, a valve bypass tool may be required to facilitate the passage of leads or other devices through the hemostasis valve. Employing valve bypass tools known in the art can increase the time associated with a medical procedure such as the implantation of a lead. Also, the removal of valve bypass tools known in the art from about an implanted lead can disrupt lead placement.

There is a need in the art for a slittable delivery device assembly for a cardiac surgical device that will reduce or eliminate the hub-to-shaft transitional jerk and reduce the potential for lead or cardiac surgical device displacement or dislodgement during removal of a delivery device assembly. There is also a need in the art for a valve bypass tool that reduces the time and complexity associated with the passage of a lead or cardiac surgical device through a hemostasis valve and reduces the potential for lead or cardiac surgical device displacement or dislodgement during the removal of the valve bypass tool. There is also a need in the art for methods of manufacturing the slittable delivery assembly, the valve bypass tool, and kits including the delivery device assembly and/or valve bypass tool.

BRIEF SUMMARY OF THE INVENTION

An assembly for the delivery of a cardiac surgical device is disclosed herein. In one embodiment, the assembly includes a slittable delivery device and a bypass assembly. The slittable delivery device may include a hub, a shaft integrated into the hub and forming at least a segment of the circumferential surface of the hub, and a hemostasis valve contained substantially within the hub. The bypass assembly may include a cap and a valve bypass tool. The cap may be on a proximal end of the hub and may include an opening in the cap extending radially outward from a point near a radial center of the cap through a circumferential edge of the cap. The valve bypass tool may be operably coupled to the cap and may include a longitudinally extending open channel.

A slittable delivery device for the delivery of a cardiac surgical device is disclosed herein. In one embodiment the delivery device includes a shaft, a hub and a valve bypass assembly. The shaft may be formed of at least a first material. The hub may be coupled to the shaft and may include a wall including a first wall segment and a second wall segment. The first wall segment may include at least the first material and the second wall segment may include at least a second material that is at least one of harder and more rigid than the first material or softer and less rigid than the first material. The valve bypass assembly may be operably coupled to a proximal end of the hub.

A slittable delivery device for the delivery of a cardiac surgical device is disclosed herein. In one embodiment, the delivery device includes a shaft, a hub coupled to a proximal end of the shaft, a consistent slitting medium extending generally the lengths of the shaft and hub, a hemostasis valve coupled to the hub, and a valve bypass tool extendable into the hemostasis valve.

Disclosed herein is a medical kit for the delivery of at least one of an implantable cardiac electrotherapy lead, an inner catheter, an outer sheath, a stylet, a guidewire and a sensor. In one embodiment, the medical kit includes a slittable delivery device, a valve bypass tool, and a package. The slittable delivery device may include a shaft, a hub coupled to a proximal end of the shaft, and a consistent slitting medium extending generally the lengths of the shaft and hub. The valve bypass tool may include a longitudinally extending slot. The package may enclose the slittable delivery device and the valve bypass tool.

Disclosed herein is a hemostasis valve bypass tool. In one embodiment, the bypass tool may include a proximal end, a distal end and a shaft extending distally from the proximal end. The shaft may include a channel defined in the shaft and extending longitudinally along the shaft between the proximal and distal ends.

Disclosed herein is a medical kit for the delivery of at least one of an implantable cardiac electrotherapy lead, an inner catheter, an outer sheath, a stylet, a guidewire and a sensor. In one embodiment, the medical kit may include the aforementioned hemostasis valve bypass tool, a slittable delivery device and a package enclosing the slittable delivery device and the valve bypass tool. The slittable delivery device may include a shaft, a hub coupled to a proximal end of the shaft, and a consistent slitting medium extending generally the lengths of the shaft and hub.

While multiple embodiments are disclosed, still other embodiments of the present invention will become apparent to those skilled in the art from the following Detailed Description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

DETAILED DESCRIPTION

Figure 1:
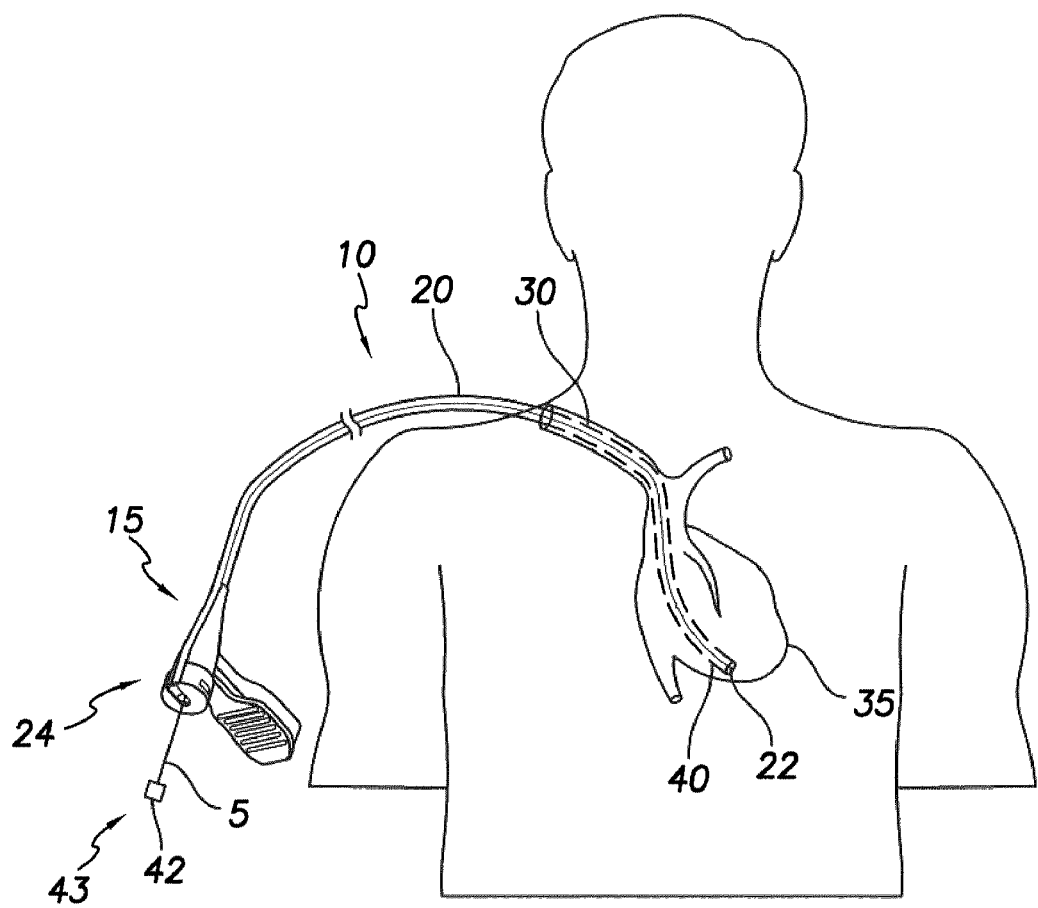
FIG. 1 is a diagrammatic view showing a slittable delivery device according to the present disclosure as it may be used for delivery of a cardiac surgical device.

The present disclosure describes a slittable delivery device 10 for a cardiac surgical device 5, e.g. an implantable medical lead, an inner catheter or outer sheath, a stylet, a guidewire, a sensor or other accessories or devices typically delivered via a catheter or sheath. The delivery device 10 may be a delivery catheter or sheath 10 having a tubular shaft 20 and a hub 15 on a proximal end 24 of the device 10. The delivery device 10 includes a lumen extending the length of the delivery device 10 and which provides a passageway for the surgical device 5 to enter the body, for example, the heart during implantation of a lead 5. Upon placement of the surgical device 5, the delivery device 10 is removed from about the surgical device 5 via slitting of the delivery device 10 along its length.

In one embodiment, the tubular shaft 20 is integrated into the hub 15 such that a wall 7 of the shaft 20 forms a longitudinally extending strip of the wall 125 of the hub 15 the entire longitudinal length of the hub wall 125 from a most proximal end 16 of the hub 15 to a most distal end 17 of the hub 15. Thus, in one embodiment, the material forming the shaft 20 may be considered to extend the entire length of the device 10 uninterrupted and fully accessible to a cutting/slicing/slitting tool 45, even through the entire length of the hub 15. When using the tool 45 to slit the delivery device 10 along its entire length, including the full lengths of the shaft 20 and hub 15, the tool 45 may encounter only the shaft material without encountering hub material, enabling the delivery device 10 to be slit and removed from about the cardiac surgical device 5 without disrupting the surgical device 5. The hub 15 with its integrated longitudinally extending shaft strip 23 reduces the hub-to-shaft transitional jerk that may occur with other delivery devices, thereby reducing the complications associated with dislodging the placed lead or other cardiac surgical device, such as increased procedure time or damage to cardiac tissue.

In one embodiment, a hemostasis valve 25 is integrated into the hub 15. An integrated hemostasis valve 25 may further reduce the time required for, and risk associated with, the procedure because preparation steps, such as slitting or otherwise removing the valve 25 prior to removal of the device 10, are not required. In one embodiment, a cap 30 may retain the hemostasis valve 25 within the hub 15.

In one embodiment, the slittable delivery device 10 may include a cap 30. As discussed in more detail below with reference to FIGS. 9-16, in some embodiments, the cap 30 may be a component of a bypass assembly 302. Together with the slittable delivery device 10, the bypass assembly 302 may be a component of a slittable delivery device assembly 300. Thus, the slittable delivery device assembly 300 may include a slittable delivery device 10 and a bypass assembly 302 including a cap 30 and a valve bypass tool 305. The slittable delivery device assembly 300 may also be a component of a kit 600.

As discussed below with reference to FIGS. 17-18, in one embodiment, the slittable delivery device 10 may include a cap 30 and the valve bypass tool 305 may be a separate tool, which in some embodiments, may be reusable during a medical procedure. The slittable delivery device with its cap and integral hemostasis valve may be provided with the separate valve bypass tool 305 in a kit 600.

In one embodiment, the bypass assembly 302 does not hinder access to the slittable delivery device 10. That is, the bypass assembly 302 may be integrated into the slittable delivery device 10 such that the entire slittable delivery device assembly 300 may be removed without disrupting the placed lead or other cardiac surgical device. The slittable delivery device assembly 300 and, more specifically, the bypass assembly 302 may reduce the time to insert leads and other devices into the hemostasis valve because a physician will not have to pick up a separate bypass tool. Also, the bypass tool 305 of the bypass assembly 302 does not have to be peeled, slit or otherwise opened up, the bypass tool 305 having a longitudinal channel 350 that allows the lead or other device to simply be removed from the bypass tool 305 (e.g., the lead or other device may simply fall out of the channel 350). Since the tool 305 does not have to be peeled, slit or otherwise destroyed to facilitate the removal of the lead or other device from within the tool 305, the tool 305 may be reused in some embodiments.

The assembly 300 may reduce the time required for, and risk associated with, an implantation procedure because the assembly 300 allows for the quick removal of the assembly 300 from about the implanted lead while reducing the likelihood of disrupting the implanted lead. Such an assembly 300 also offers a physician the ability to insert and maneuver a cardiac surgical device 5 in a range of sizes through the valve 25 without requiring a secondary insertion tool.

For a general discussion of a slittable delivery device 10 utilized to deliver a cardiac surgical device 5, reference is first made to FIG. 1, which is a diagrammatic view of the delivery device 10 as it may be used during delivery of a cardiac surgical device 5, such as an implantable cardiac electro-therapy lead. The following discussion is given in the context of the cardiac surgical device 5 being a lead 5. However, the cardiac surgical device 5 may be any other type of device 5, including, for example, outer sheaths or inner catheters, guidewires, stylets, sensors, etc. The delivery of such surgical devices 5 via the delivery device 10 will be similar to that described below with respect to the delivery of a lead 5.

As previously mentioned and as can be understood from FIG. 1, the delivery device 10 may be a delivery catheter or sheath 10 having a tubular shaft 20 and a hub 15 on a proximal end 24 of the device 10. The hub 15 may include an integral hemostasis valve 25. During a lead implantation procedure, for example, the tubular shaft 20 is inserted into the patient's heart 35 via the subclavian vein 30 or other appropriate entry point.

Once the shaft 20 is in position, a cardiac surgical device 5 may be inserted therethrough. For example, once the shaft 20 is in position, a lead 5 may be inserted through the hemostasis valve 25 in the hub 15 and through the lumen of the shaft 20 so the lead tip 40 at the distal end of the lead 5 may be guided into position in the heart 35.

The lead 5 includes a proximal end 43. In one embodiment, the proximal end 43 of the lead 5 includes an electrical connector 42 for mechanically and electrically coupling the lead proximal end to a pulse generator, such as a pacemaker or ICD. The electrical connector 42 is of a size that prevents the delivery device 10 from being proximally withdrawn from about the lead 5. The length of the lead 5 may present an equal hindrance. Once the lead 5 is implanted or placed into position, as appropriate, the device 10 may be slit to allow the delivery device 10 to clear the connector 42 or proximal end 43 as the delivery device 10 is removed from about the lead 5.

As mentioned above and described in more detail below, the material forming the shaft 20 extends into the hub 15 to form at least a longitudinal strip of the hub wall 125. Thus, the slit path for slitting the entire delivery device 10, including the entire shaft 20 and entire hub 15, extends along shaft material and does not encounter hub material, or at least any significant amount of hub material. With respect to the slitting path 23, the delivery device 10 has no hub-to-shaft transition, resulting in a delivery device 10 that may be slit with low and consistent slit forces along the entire length of the delivery device 10, substantially reducing, if not completely eliminating, the transition jerk normally associated with slitting through the hub-to-shaft transition of devices known in the art. Advantageously, the chance of dislodging or disrupting the position of the implanted lead 5 is reduced or eliminated. Additionally, because the shaft is integrated into the hub, the delivery device 10 does not require removal of the hub in order to slit the shaft. In some embodiments, the hub 15 may include an integrated valve and cap configured to be slit, thereby increasing the efficiency and reducing the risk associated with employing the device 10.

Figure 2:
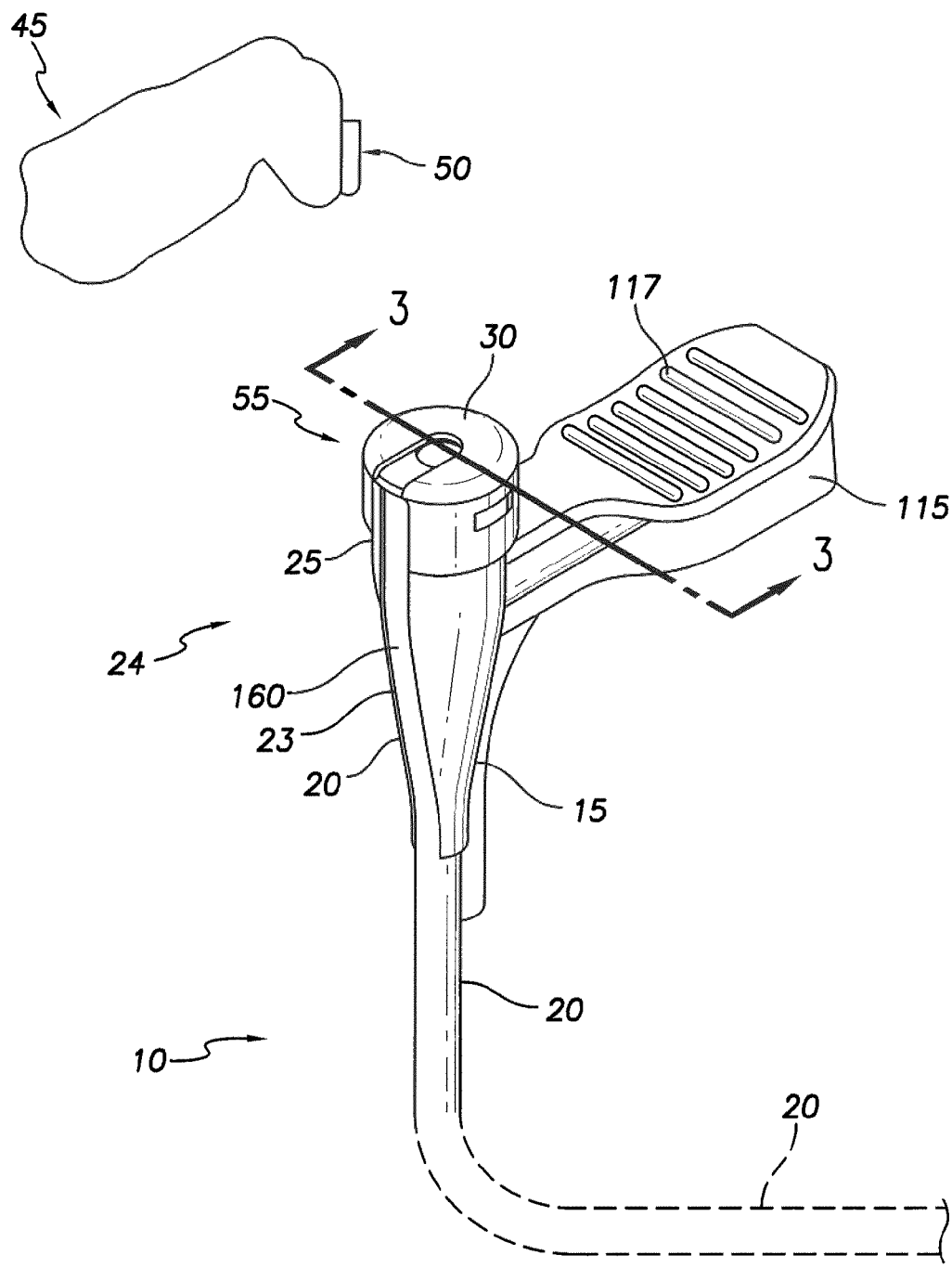
FIG. 2 is an embodiment of the slittable delivery device of FIG. 1, wherein a slitting tool is also shown.
Figure 3:
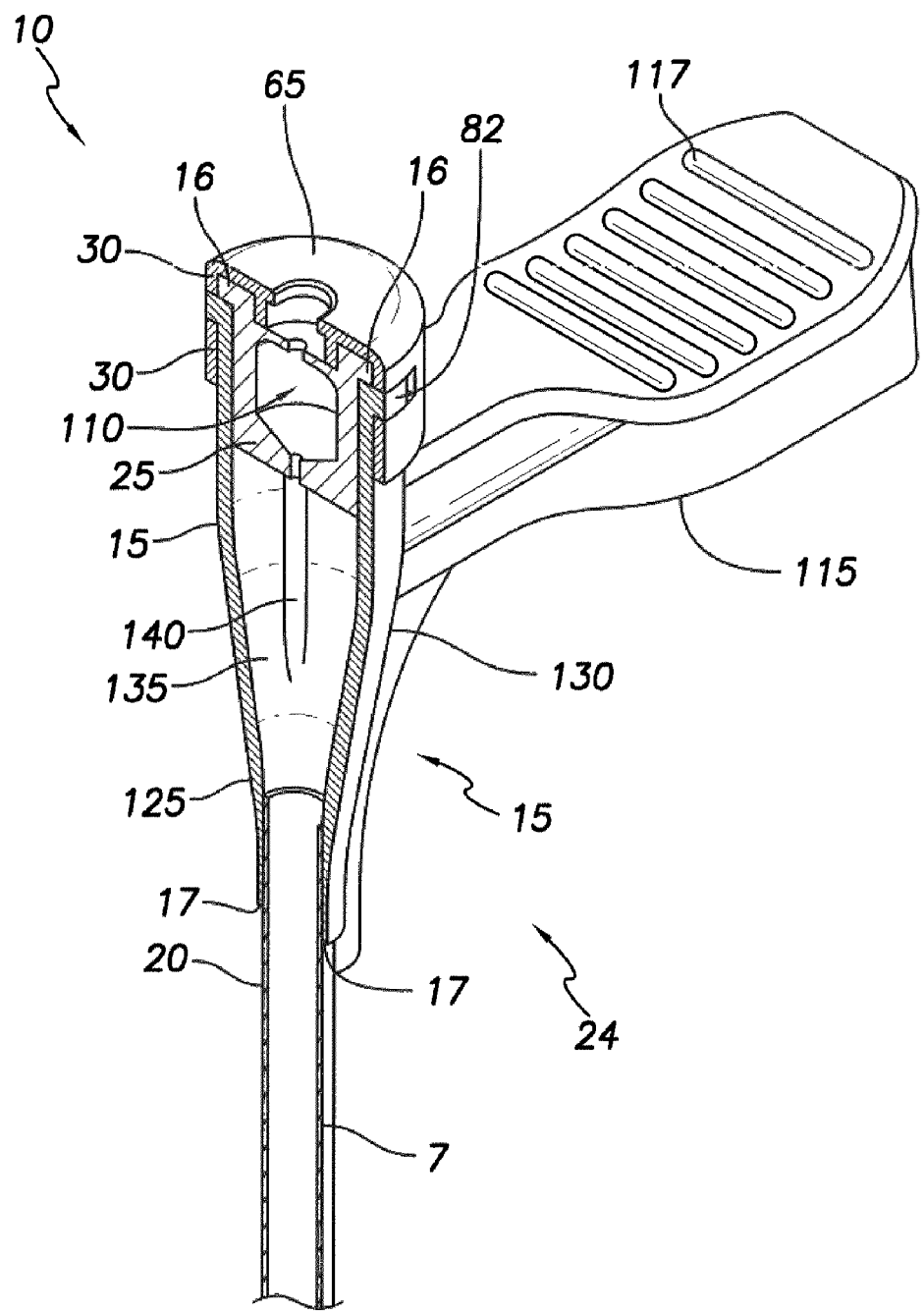
FIG. 3 is a cross-sectional elevation of the device as taken along section line 3-3 of FIG. 2.
Figure 6A:
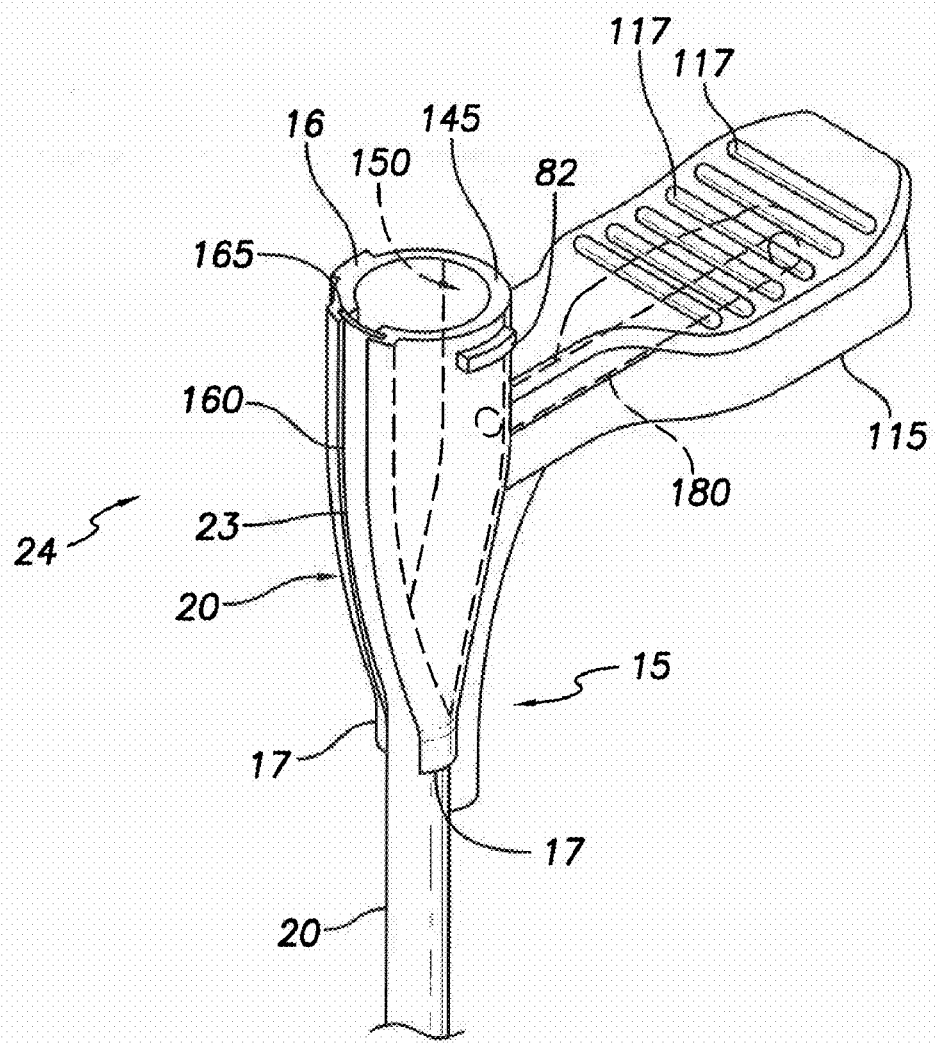
FIG. 6A is a transparent view of one embodiment of the hub and sheath of FIG. 2, wherein the valve and cap are hidden for clarity purposes.
Figure 6B:
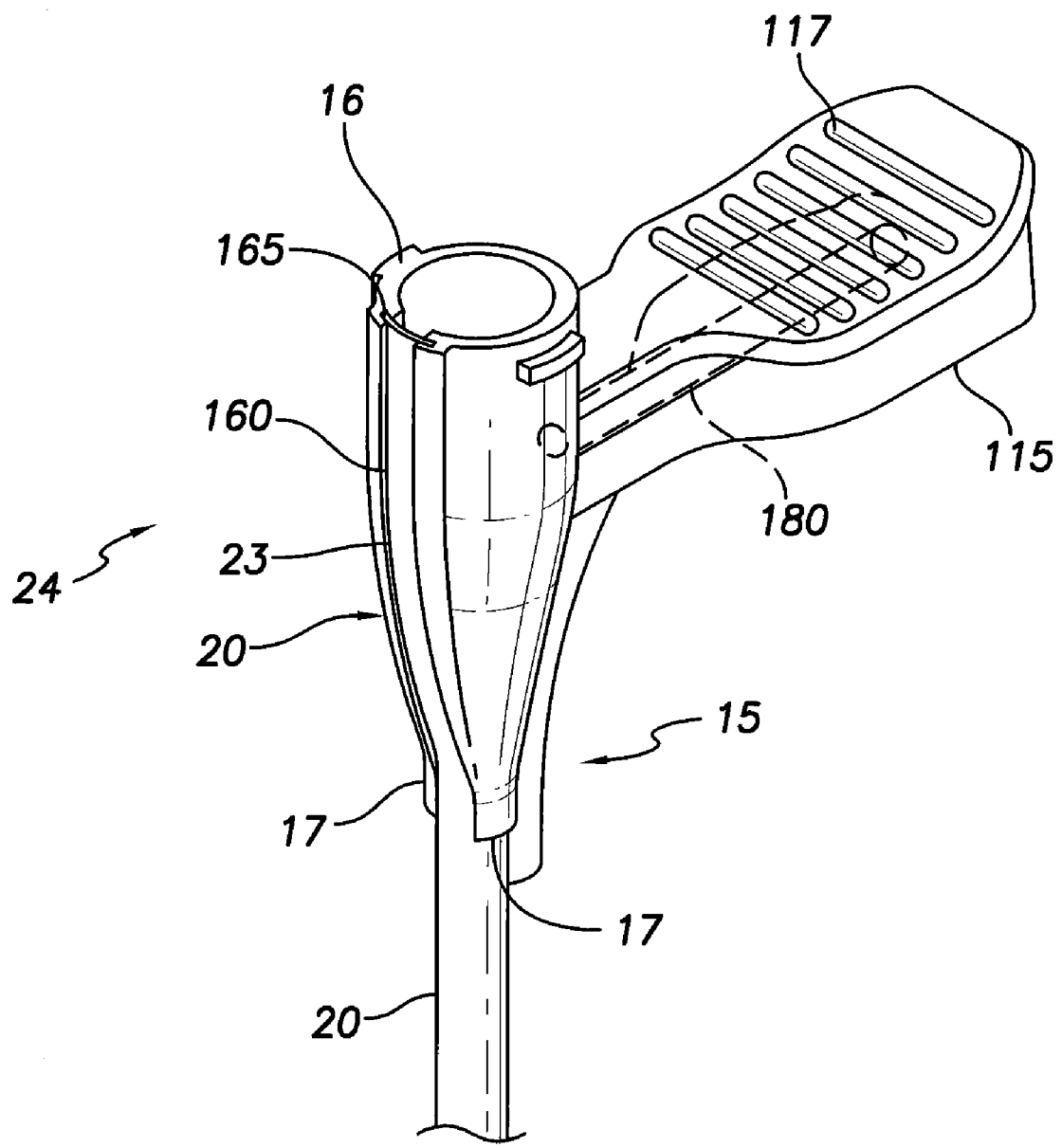
FIG. 6B is a transparent view of a second embodiment of the hub and sheath of FIG. 2, wherein the valve and cap are hidden for clarity purposes.
Figure 7A:
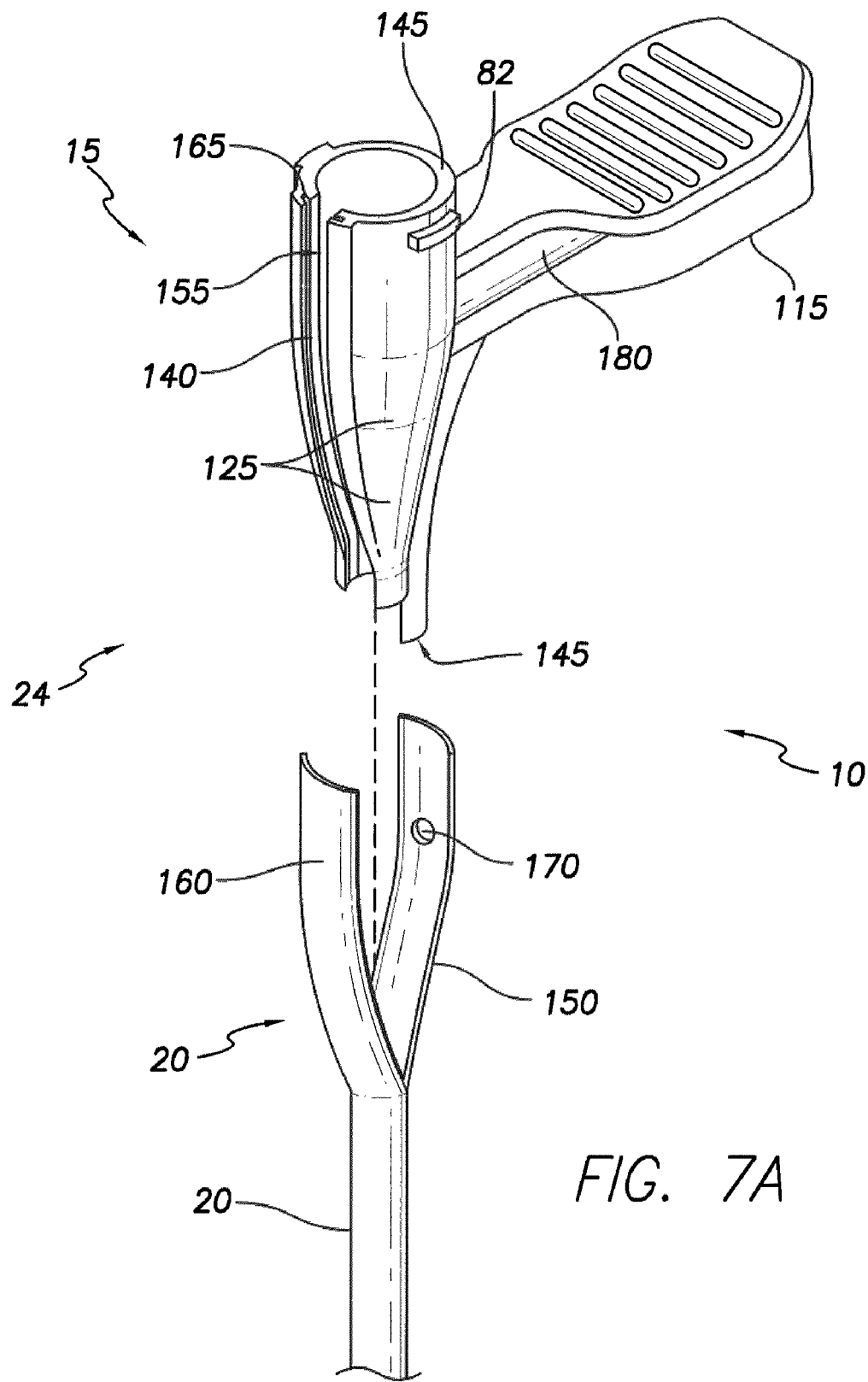
FIG. 7A is an exploded view of one embodiment of the delivery device of FIG. 6A.
Figure 7B:
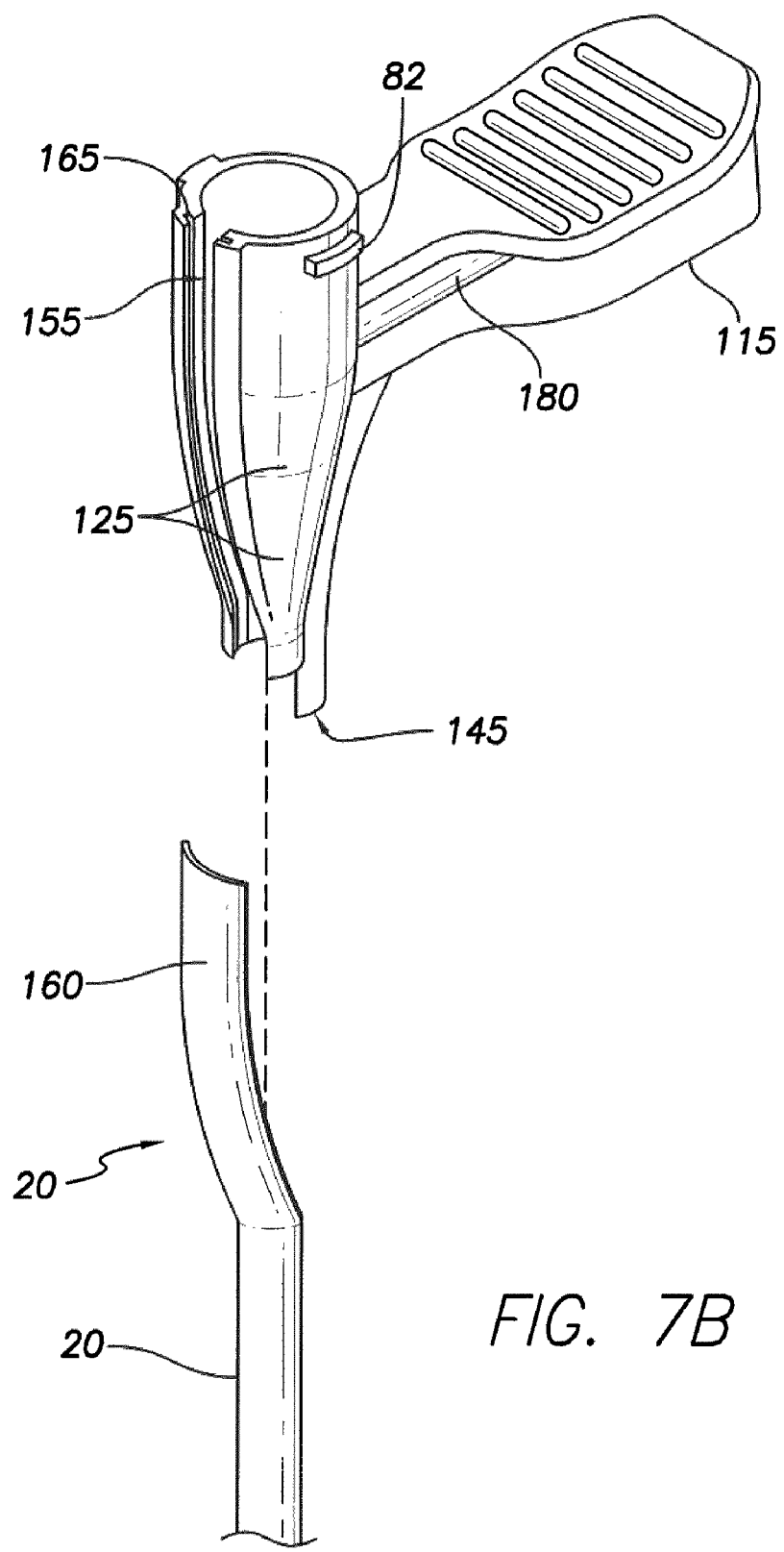
FIG. 7B is an exploded view of a second embodiment of the delivery device of FIG. 6B.
Figure 8A:
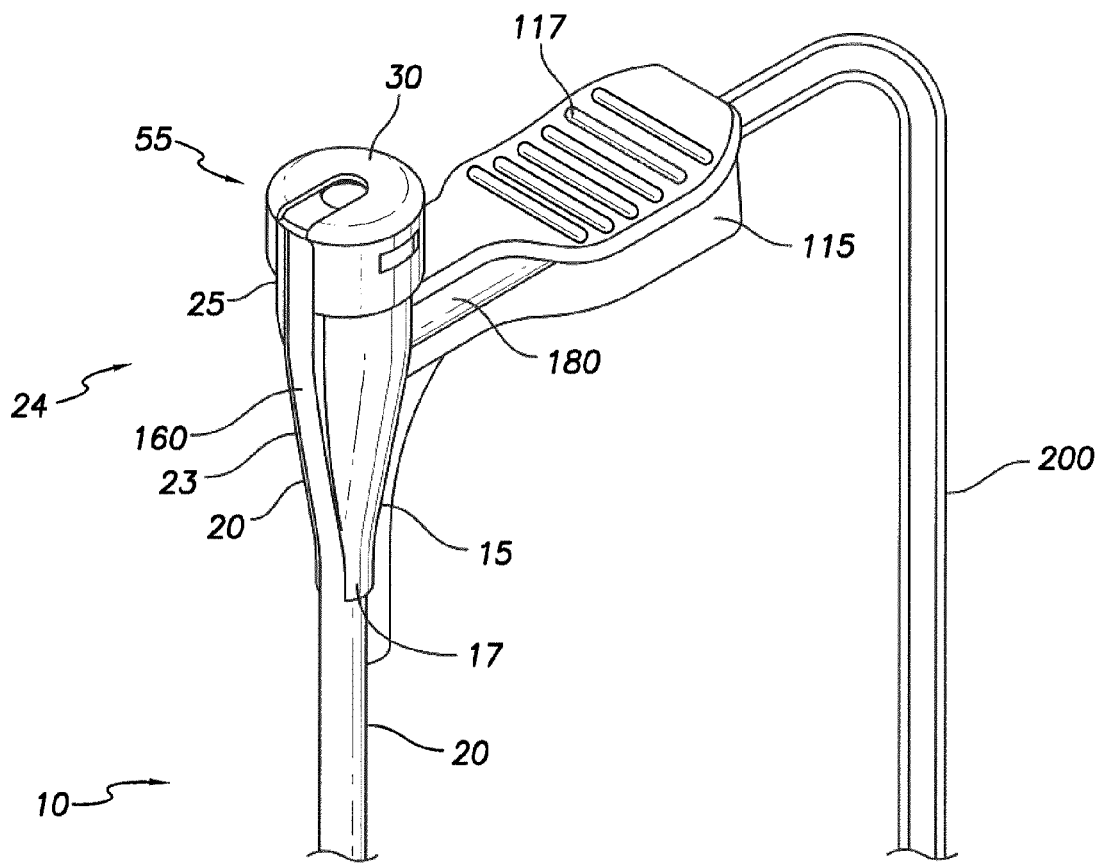
FIG. 8A is an embodiment of the slittable delivery device of FIG. 1, wherein a side port extension tube is also shown.
Figure 8B:
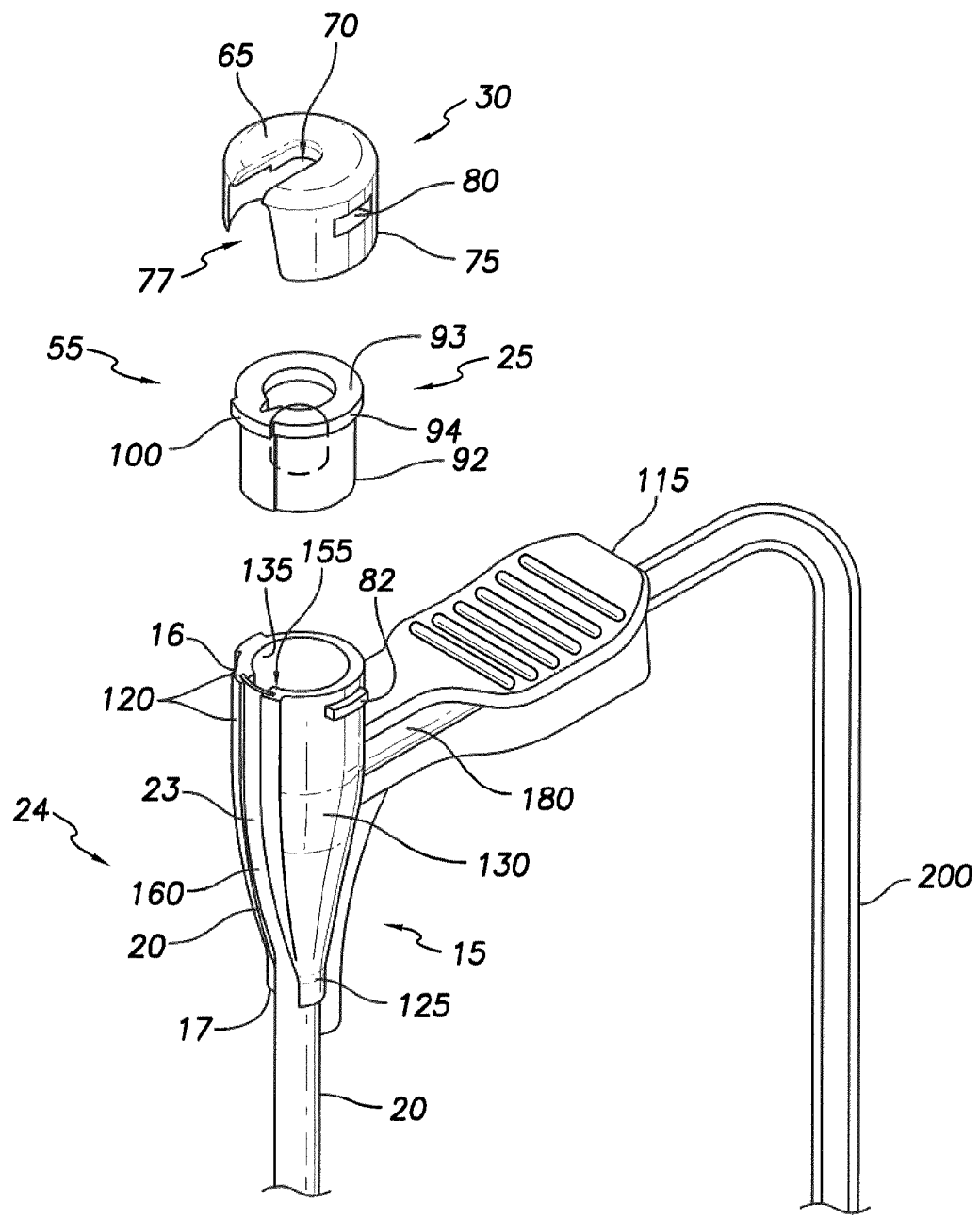
FIG. 8B is a partially exploded view of the slittable delivery device of FIG. 8A.

For a detailed discussion of the slittable delivery device 10 and the components of the delivery device 10, reference is now made to FIGS. 2-8B. FIG. 2 is an isometric view of the slittable delivery device 10 and a slitter 45, and FIG. 3 is a cross-sectional elevation of the delivery device 10 as taken along section line 3-3 of FIG. 2. FIGS. 4A and 4B are partially exploded views of some embodiments of the hub end 24 of the delivery device 10, and FIGS. 5A and 5B are isometric views of some embodiments of the valve 25. FIGS. 6A and 6B are transparent views of some embodiments of a hub 15 and sheath 22, and FIGS. 7A and 7B are exploded views of some embodiments of the hub 15 and sheath 22 of FIGS. 6A and 6B, respectively. FIG. 8A is an embodiment of the slittable delivery device of FIG. 1, wherein a side port extension tube is also shown. FIG. 8B is a partially exploded view of the slittable delivery device of FIG. 8A.

As can be understood from FIGS. 2-4B, the slittable device 10 includes the shaft 20 and the hub 15. In some embodiments, the device 10 further includes a valve 25 and a cap 30, wherein the cap 30 retains the valve 25 inside the hub 15 to form a hub with an integral hemostasis valve.

As indicated in FIG. 2, the device 10 may also include a slitting tool 45 for slitting/cutting the device 10, including the shaft 20 and the hub 15. The slitter 45 includes a blade 50 or other suitable cutting mechanism. In alternative embodiments, the slittable delivery device 10 may be slit with another suitable cutting or slitting tool.

As shown in FIGS. 2-4B, the proximal end 24 of the device 10 includes the hub 15, which is mounted on the proximal end of the shaft 20. The hub 15 includes a proximal end 16 and a distal end 17. The hub 15 may be configured such that the hub proximal end 17 may receive and couple with a hemostasis valve such as those commonly known in the art. Alternatively, the hub 15 may be equipped with an integral hemostasis valve 25 located within the hub 15 and maintained in place via a cap 30 configured to couple with the hub proximal end 16.

Figure 4A:
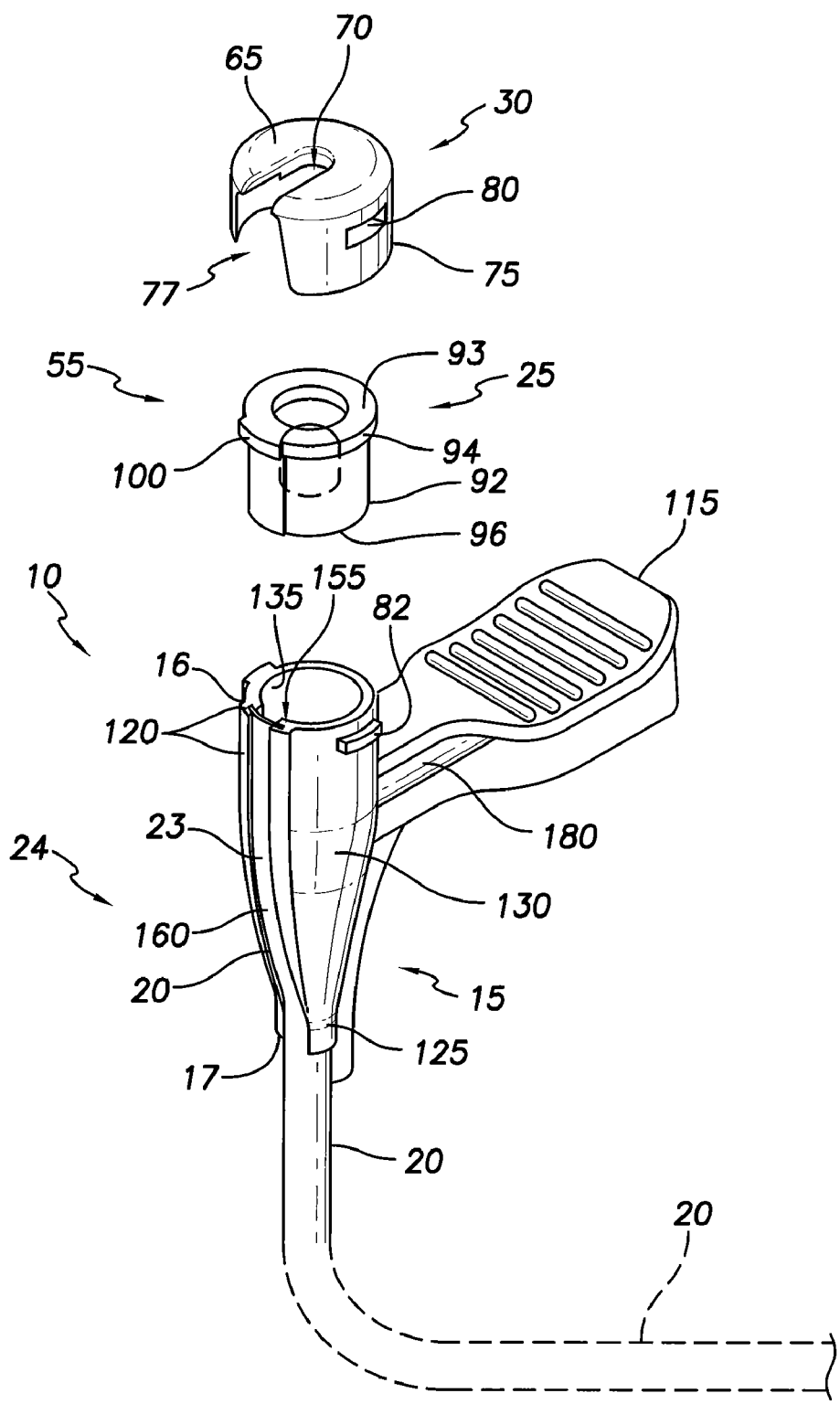
FIG. 4A is a partially exploded view of one embodiment of the hub end of the delivery device of FIG. 1.
Figure 4B:
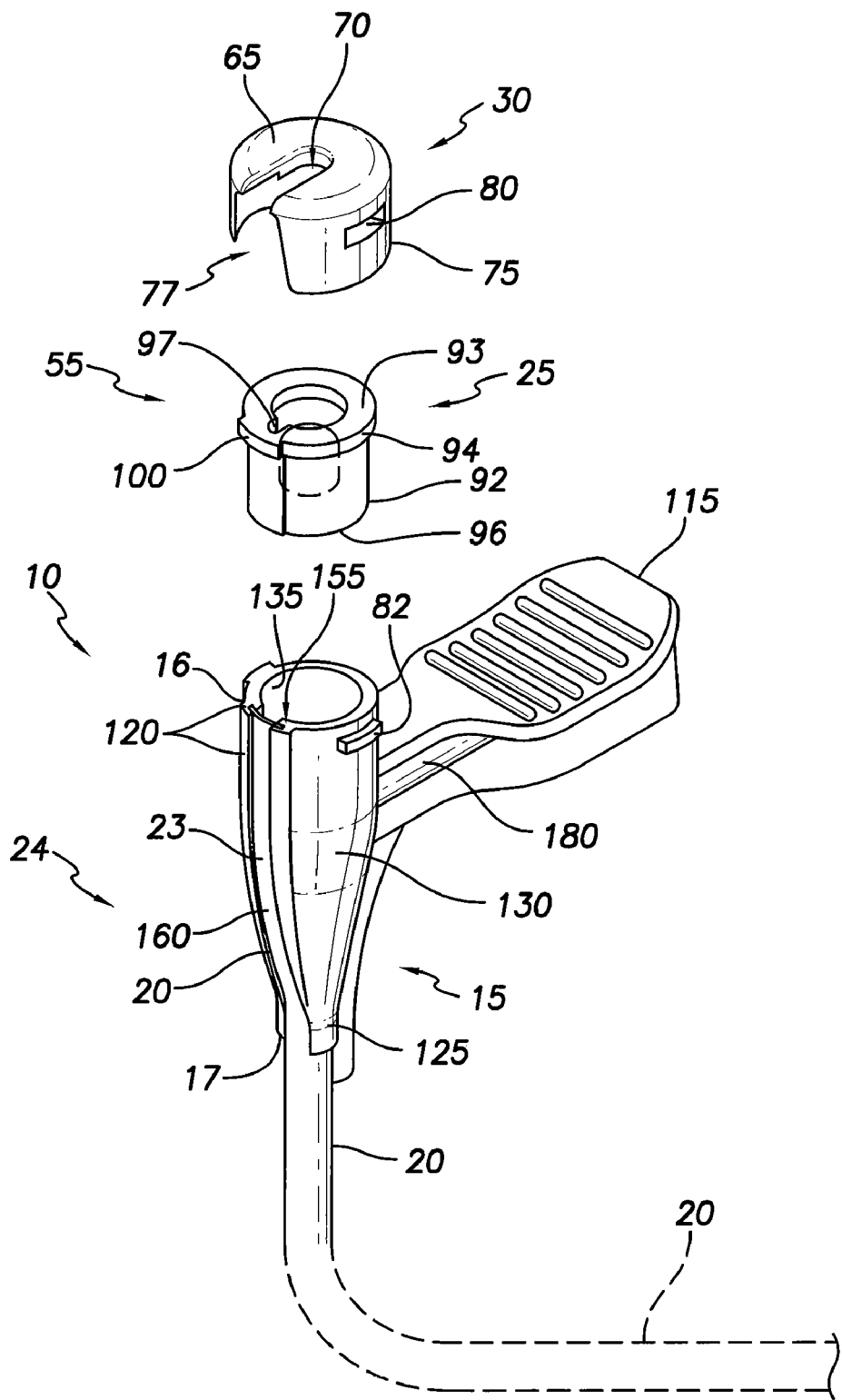
FIG. 4B is a partially exploded view of a second embodiment of the hub end of the delivery device of FIG. 1.

As indicated in FIGS. 2, 4A and 4B, the cap 30 is generally an open-ended cylindrical shape and includes a proximal or surgical device receiving face 65 and a lateral generally cylindrical wall 75. The cap 30 is configured to generally receive the hub 15, thereby partially enclosing the proximal face of the valve 25 and maintaining the valve within the hub 15 to create a fluid tight seal. The cap 30 may be made of a generally rigid, hard material, for example, acrylonitrile-butadiene-styrene ("ABS"), polyether block amides ("PEBAX"), high density polyethylene ("HDPE"), polycarbonate, nylon, or etc.).

As indicated in FIGS. 2, 4A and 4B, the surgical device receiving face 65 of the cap 30 is generally circular and includes a U-shaped opening 70. The U-shaped opening 70 is configured to receive the distal end of the cardiac surgical device 5. The U-shaped opening 70 also exposes a portion of the valve 25 such that a slittable valve 25 may also be slit during removal of the device 10. Also, the U-shaped opening 70 allows for the cap 30 to be removed from about the cardiac surgical device 5 once the surgical device 5 is implanted or otherwise positioned. That is, the cap 30, which may be coupled to the valve 25, may be removed from about the surgical device 5 during or after slitting of the delivery device 10.

As shown in FIGS. 2, 4A and 4B, the wall 75 of the cap 30 includes an arcuate opening 77. The arcuate opening 77 nearly intersects the proximal face 65 of the cap 30 at the open end of the U of the U-shaped opening 70 to merge with the U-shaped opening 70. The arcuate opening 77 is configured to expose a proximal portion of the hub 15 and the shaft 20 and, more specifically, to expose the slit path or strip 23 extending the length of the hub 15, thereby allowing the tool blade 50 to access the slit strip 23. In one embodiment, the arcuate opening 77 may also expose a portion of a slittable valve, thereby aiding in slitting of a slittable valve.

As can be understood from FIGS. 2-4B, the wall 75 of the cap 30 also includes tab receiving openings 80. The openings 80 are configured to receive hub tabs 82 defined on the outer circumference of the hub 15, thereby forming a bayonet lug type connection arrangement. In one embodiment, the openings 80 are rectangular. In other embodiments, the openings 80 may be a different shape, such as circular or other suitable shape as needed to conform to the tabs 82 defined on the hub 15. In one embodiment, there are two tab receiving openings 80. In alternative embodiments, there may be less than two openings 80 or there may be more than two openings 80.

In some embodiments, the delivery device 10 includes an integrated or internal hemostasis valve 25 configured to be received in the hub 15 and maintained in place by the cap 30, as discussed above. In other embodiments, the delivery device 10 does not include the integrated hemostasis valve 25 or cap 30. Instead, the proximal end 16 is configured to receive an external hemostasis valve as commonly used in the art.

As shown in FIGS. 4A-5B, in some embodiments, the integral hemostasis valve 25 includes an outer housing or body component 92 and an inner valve component 90. The valve 25 is generally cylindrical and is configured to mate with and be received within the hub 15, thereby creating a fluid tight seal. In one embodiment, the valve 25 is formed from a generally resilient, soft material, e.g., (e.g. silicone rubber or other elastomer).

Figure 5A:
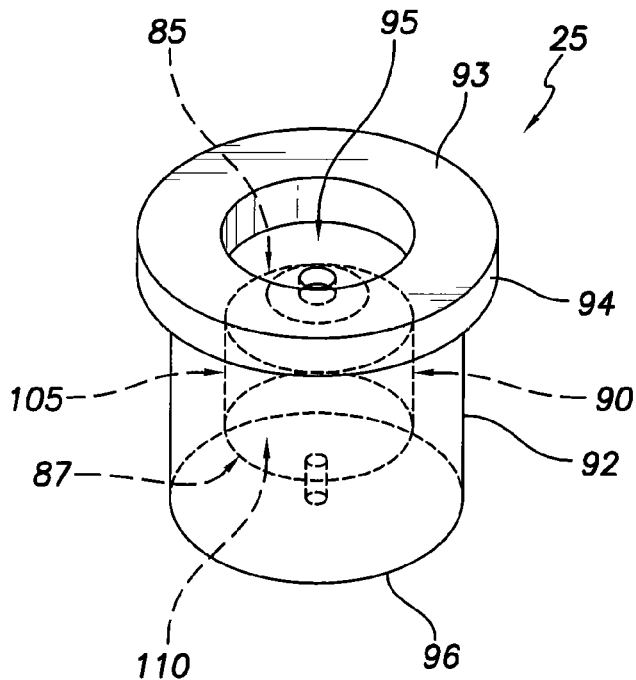
FIG. 5A is an isometric view of one embodiment of the valve of FIG. 4A.
Figure 5B:
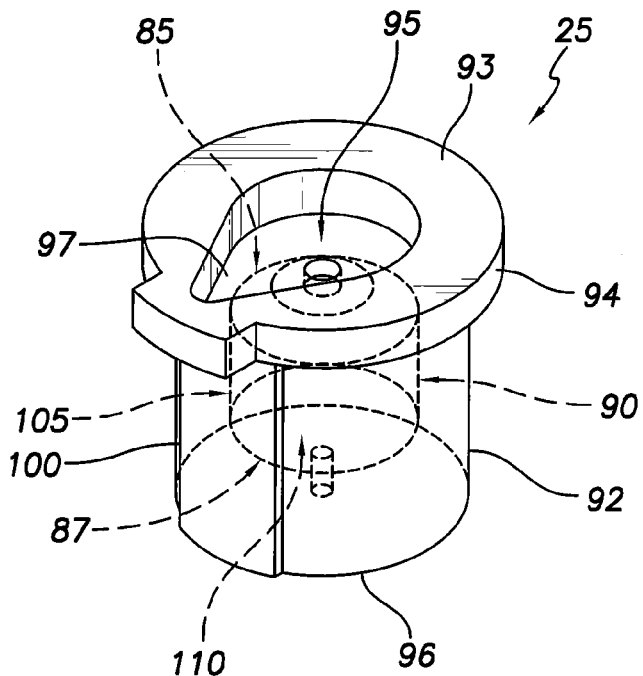
FIG. 5B is an isometric view of a second embodiment of the valve of FIG. 4B.

As indicated in FIGS. 4A-5B, the housing 92 of the valve 25 includes a cap side 93 that is configured to matingly receive the cap 30 and a hub side 96 that is configured to be received in the hub 15. The cap side 93 of the housing 92 is generally circular or disc-shaped and includes an opening 95 defined therein. In one embodiment, the circumference of the cap side 93 of the housing 92 is greater than the circumference of the housing 92, thereby forming a rim or lip 94. In alternative embodiments, the circumference of the cap side 93 is approximately equal to the circumference of the housing 92. In one embodiment, as shown in FIGS. 4B and 5B, the opening 95 may include a v-notch 97, which may help to align the slitter and provide for ease of slitting.

As can be understood from FIGS. 4A, 4B and 5B, in some embodiments, the outer circumference of the cap side 93 of the housing 92 may include a valve tab 100. The valve tab 100 extends from the outer circumference of rim 94 of the cap side 93 on approximately the same plane as the cap side. In one embodiment, as shown in FIG. 5B, the valve tab 100 extends from the outer circumference of rim 94 of the cap side 93 on approximately the same plane as the cap side 93 and extends along a portion of the outer circumference of the housing 92 of the valve 25 between the cap side 93 and the hub side 96. Referring now to FIGS. 4A-5B, in some embodiments, the valve 25 may be coupled to the cap 30 and together, the valve 25 and cap 30 are coupled to the hub 15. The valve tab 100 may provide a feature for grasping to insert the valve into the hub or to facilitate the removal from the hub during manufacture. The valve tab 100 may also help to facilitate the seal between the cap 30, valve 25 and hub 15. As indicated in FIGS. 2 and 5A, in an alternative embodiment, the outer circumference of rim 94 of the cap side 93 of the housing 92 of the valve 25 may not include a valve tab 100.

As shown in FIGS. 4A-5B, the opening 95 in the face of the cap side 93 of the valve 25 provides an entryway or passageway leading to the inner valve component 90. The inner valve component 90 includes resilient members 85, 87 and a wall 105. The resilient members 85, 87 and the wall 105 define a chamber 110 through which a cardiac electrotherapy lead or other cardiac surgical device may pass during placement of the lead or other device into the heart. The resilient members 85, 87 include a slit or other opening that may bias closed around a surgical device 5 extending through the inner valve component 90, creating a fluid tight seal about the surgical device 5.

As shown in FIGS. 2-4B and 6A-7B, the proximal end 24 of the delivery device 10 includes a hub 15 with an integrated shaft 20 forming a longitudinally extending hub slitting strip 23 in the hub wall 125. As can be understood from FIGS. 6A-7B, in some embodiments, to assist in the integration of the shaft 20 into the hub 15 during manufacture, the proximal end of the shaft 20 may be split or divided along a longitudinal centerline prior to being molded or formed into the hub. One of the shaft segments resulting from the longitudinal dividing of the shaft proximal end is an exposed portion 160 and the other an unexposed portion 150 imbedded within the material forming the hub 15. As indicated in FIGS. 6B and 7B, in some embodiments, the proximal end of the shaft 20 includes only a single shaft segment, the exposed portion 160.

As illustrated in FIGS. 6A-7B, the unexposed portion 150 and exposed portion 160 of the shaft 20, if present, are integrated into the hub 15 such that the exposed portion 160 is aligned with the hub opening 155 and forms at least a segment of the circumferential surface of the hub 15, as discussed in more detail below. In one embodiment, the proximal end of the shaft 20 extends to the proximal end 16 of the hub 15. In other embodiments, the proximal end of the shaft 20 may extend to an alternative location within the hub 15 somewhere between the hub proximal end 16 and hub distal end 17. The shaft 20 may be formed of polytetrafluoroethylene ("PTFE"), PEBAX, Nylon, polyurethane, fluorinated ethylene propylene ("FEP") or etc. or a combination of these materials supported by a reinforcement braid pattern.

As indicated in FIGS. 4A and 4B, and 6A-8B, the hub 15 may include a handle 115 with a portal 180 extending from the interior of the hub 15 to daylight at the free end of the handle 115. As shown in FIG. 7A, the unexposed portion 150 of the shaft 20 may include a portal opening 170. The portal opening 170 generally corresponds to the opening in the interior of the hub formed by the portal 180 in the hub handle 115.

As shown in FIGS. 3, 4A, 4B, and 6A-8B, the hub 15 includes a body 125 which may be a generally conical wall with an outer circumferential surface 130 and an inner circumferential surface 135. The outer surface 130 of the body 125 may include the hub tabs 82 and the handle 115. The hub tabs 82 are configured to be received by the hub receiving openings 80 defined in the cap 30, thereby creating a seal between the valve 25, cap 30 and the hub 15. The hub body or wall 125 may be formed of a generally rigid, hard material, for example, acrylonitrile-butadiene-styrene ("ABS"), polyether block amides ("PEBAX"), high density polyethylene ("HDPE"), polycarbonate, nylon, or etc.).

In one embodiment, the handle 115 includes a portal 180 and ridges 117 that provide a gripping surface. The portal 180 provides a passageway into the hub 15 via the handle 115 and the portal opening 170 in the shaft 20 for the delivery of fluids, such as fluoroscopy contrasts, etc. into the lumen of the device 10. As shown in FIGS. 8A and 8B, an extension tube 200, such as a PVC extension tube with a three-way stopcock valve, may be coupled to the portal 180 and may serve to deliver the fluids. The handle 115 may provide leverage or stability for the device 10 during delivery of the cardiac surgical device 5 or slitting of the delivery device 10.

As indicated in FIG. 3, in one embodiment, the inner circumference 135 of the body 125 of the hub 15 includes raised portions 140 configured to generally abut the distal end of the valve 25 and impede or stop the valve 25 from extending distally beyond a desired point in the hub 15. In other embodiments, the hub 15 may not include raised portions 140, but rather the shape or contours of the hub 15 may impede or prevent the valve 25 from distally extending beyond a desired point in the hub 15.

As can be understood from FIGS. 6A and 7A, in one embodiment, a void or space 145 is defined between the inner circumference 135 and outer circumference 130 of the hub 15. The unexposed portion 150 of the shaft 20 is received in the void or space 145. More specifically, in one embodiment, during the manufacturing process when the hub wall 125 is formed (e.g., via insert or injection molding) about the unexposed portion 150, the portion 150 defines the void or volume in the hub wall 125 in which the portion 150 resides.

As shown in FIGS. 2, 3, 4A-4B, and 6A-8B, in some embodiments, the hub 15 is generally a flat-bottomed conical shape. The body or wall 125 of the hub 15 includes slots 165 and a hub opening 155 configured to receive an exposed portion 160 of the shaft 20. The hub opening 155 may be a longitudinal gap or slot 155 defined in and extending the length of the hub wall 125 from the proximal hub end 16 to the distal hub end 17. The exposed portion 160 of the shaft 20 is received in the hub opening 155 such that the exposed portion 160 forms a longitudinally extending segment of the hub wall 125, including longitudinally extending segments of the inner and outer surfaces 130, 135 of the hub wall 125.

To secure the exposed portion 160 in place such that it forms a longitudinal segment of the hub wall 125, the lateral edges of the exposed portion 160 are received in the slots 165 bordering each wall edge of the hub wall 125 defining the hub opening 155. Similar to the creation of the void space 145 with respect to the unexposed portion 150, in one embodiment, during the manufacturing process when the hub wall 125 is formed (e.g., via insert or injection molding) about the lateral edges of the exposed portion 160, the portion 160 defines the slots 165 in the hub wall 125 in which the lateral edges of the portion 160 reside.

As can be understood from FIGS. 2-4B and 6A-8B, the shaft 20 is integrated into the hub 15 such that the shaft 20 forms a longitudinally extending segment of the hub wall 125. In one embodiment, this longitudinally extending segment of the hub wall 125 provides a slitting path extending the full length of the delivery device 10 and formed of shaft material and no hub material at all or of any significant amount. This configuration allows the delivery device 10 to be slit along its entire length without removal of the hub 15 and without a transitional jerk. Thus, in one embodiment, a physician may slit through the length of the delivery device 10 and encounter only a single slittable medium with low and consistent slit forces, thereby reducing or eliminating the shaft-to-hub transitional jerk and reducing the likelihood of disrupting the placement of the cardiac surgical device 5 upon removal of the delivery device 10.

In an alternative embodiment, as shown in FIG. 4A, the body 125 of the hub 15 may include ridges 120 extending along the edges of the hub opening 155. The ridges 120 include the slots 165, which, as discussed above, are configured to receive the lateral edges of the exposed portion 160 of the shaft 20. That is, the shaft 20 is integrated into the hub 15 at the hub opening 155 and is received in the ridges 120 with slots 165 such that the shaft 20 forms at least a longitudinal segment of the hub wall 125.

As can be understood from FIGS. 2, 3 and 6A-6B, in some embodiments, the hub opening 155 extends the length of the hub 15 and provides a small channel through which the shaft 20 may be slit. A small channel allows the hub to retain its radial strength and also provides a directional window or visual indicator to direct the physician to the slit channel. In other embodiments, the hub 15 may have a differently shaped hub opening 155 as long as the opening 155 accommodates extension of the shaft 20 into the hub 15 such that the shaft 20 may include at least a longitudinal segment of the hub wall 125.

In one embodiment, the hub may be insert injection molded or injection molded around the shaft. In an alternative embodiment, the hub may be machined or molded and then the shaft may be assembled into the hub. The valve and cap may also be assembled into or onto the hub. Once assembled, the delivery device 10 may be utilized in a medical procedure to implant or otherwise place a cardiac surgical device 5.

As can be understood from FIG. 2, and with reference to FIG. 1, the delivery device 10 is generally configured to receive a lead or other cardiac surgical device 5 at the proximal end 17 of the device 10, and the lead or other surgical device 5 may be guided through the lumen of the shaft 20 to the implant or desired location in the heart 35. Once the lead is implanted at the desired electrotherapy implant location or the surgical device is placed at the desired location, the delivery device 10 may be slit with a slitter 45 or other cutting tool and withdrawn from about the surgical device 5. As discussed above, the cap 30 and valve 25 may be coupled to the hub 15. In some embodiments, the arcuate opening 77 in the cap 30 is configured to allow passage of the slitter blade through the cap 30 and valve 25 such that removal of the cap 30 prior to slitting is not required. Also, the hemostasis valve 25 may be slit while in place within the hub 15.

The shaft integrated into the hub provides a consistent slit medium such that the cardiac surgical device is not displaced from its position or location in or near the cardiac tissue. Such a slittable device reduces the time required for the procedure by reducing the chance of dislodging the surgical device during the removal of the delivery device from about the surgical device.

While the delivery device 10 discussed above may include a hub 15, a shaft 20, a hemostasis valve 25 and a cap 30, in other embodiments, the delivery device 10 may be a component of a slittable delivery device assembly 300. The slittable delivery device assembly 300 may include a delivery device 10 and a bypass assembly 302. While in some embodiments the cap 30 may be a component of the delivery device 10, in other embodiments, such as in the slittable delivery device assembly 300, the cap 30 is a component of the bypass assembly 302.

In addition to the cap 30, in some embodiments, the bypass assembly 302 also includes a valve bypass tool 305. The bypass assembly 302 of the slittable delivery device assembly 300 does not hinder access to the slittable delivery device 10. Thus, at least in part because of the slittable nature of the hub 15 and shaft 20 of the delivery device 10, the side opening 326 of the cap 30, and the channel 350 of the bypass tool 305, the entire assembly 300 may be removed from about the implanted medical lead 5 without disrupting the implanted medical lead 5.

In some embodiments, where valve bypass assembly 302 includes the cap 30 and the valve bypass tool 305 and is an integrated part of the assembly 300 including the slittable delivery device 10. Thus, these components 30, 305 and 10 forming the integrated assembly 300 may removed from about the implanted lead 5 at the same time and as an integrated whole. In other embodiments, where the cap 30 is a part of the slittable delivery device 10 and the valve bypass tool 305 is a separate tool for use with the slittable delivery device 10, the valve bypass tool 305 may be removed from the slittable delivery device 10 and from about the lead 5 separate from the removal of the slittable delivery device 10. In such an embodiment, the separate valve bypass tool 305 may be reused as different devices are inserted into the hemostatis valve of the hub of the slittable delivery device 10 over the course of the implantation of the lead 5.

Figure 9:
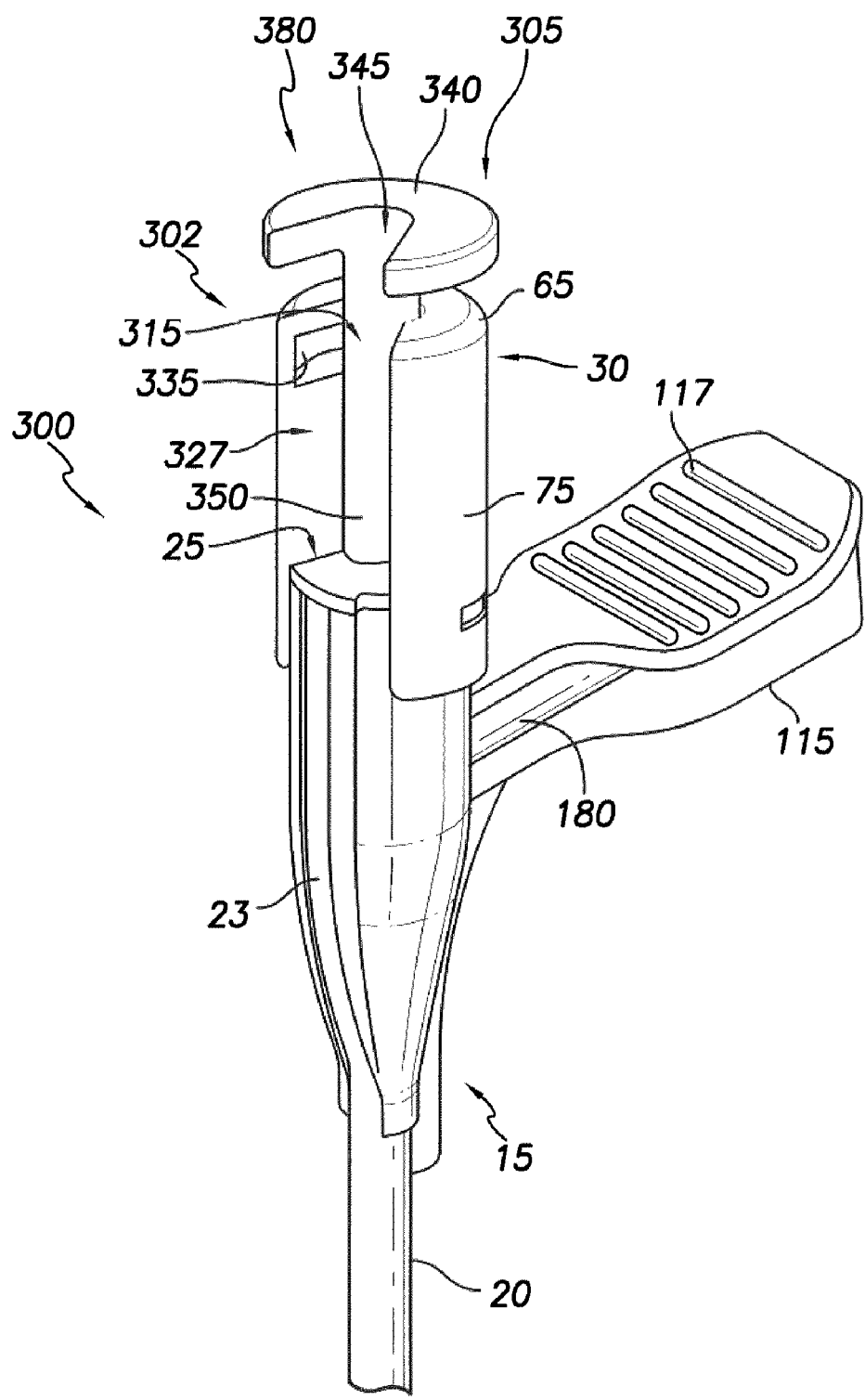
FIG. 9 is an embodiment of a slittable delivery device assembly comprising the slittable delivery device of FIG. 1.
Figure 13A:
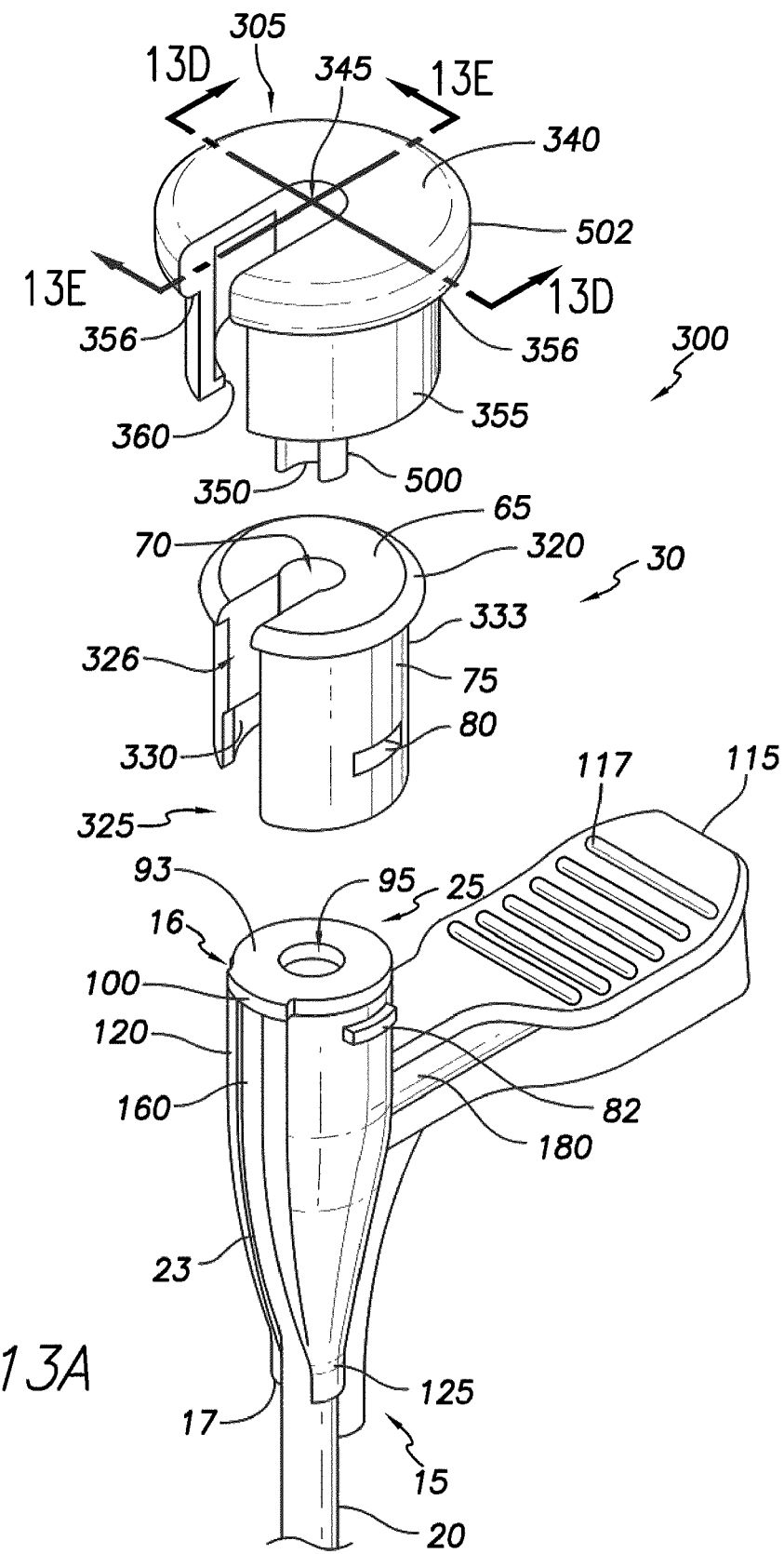
FIG. 13A is the same view as FIG. 10A, except of another embodiment.
Figure 13B:
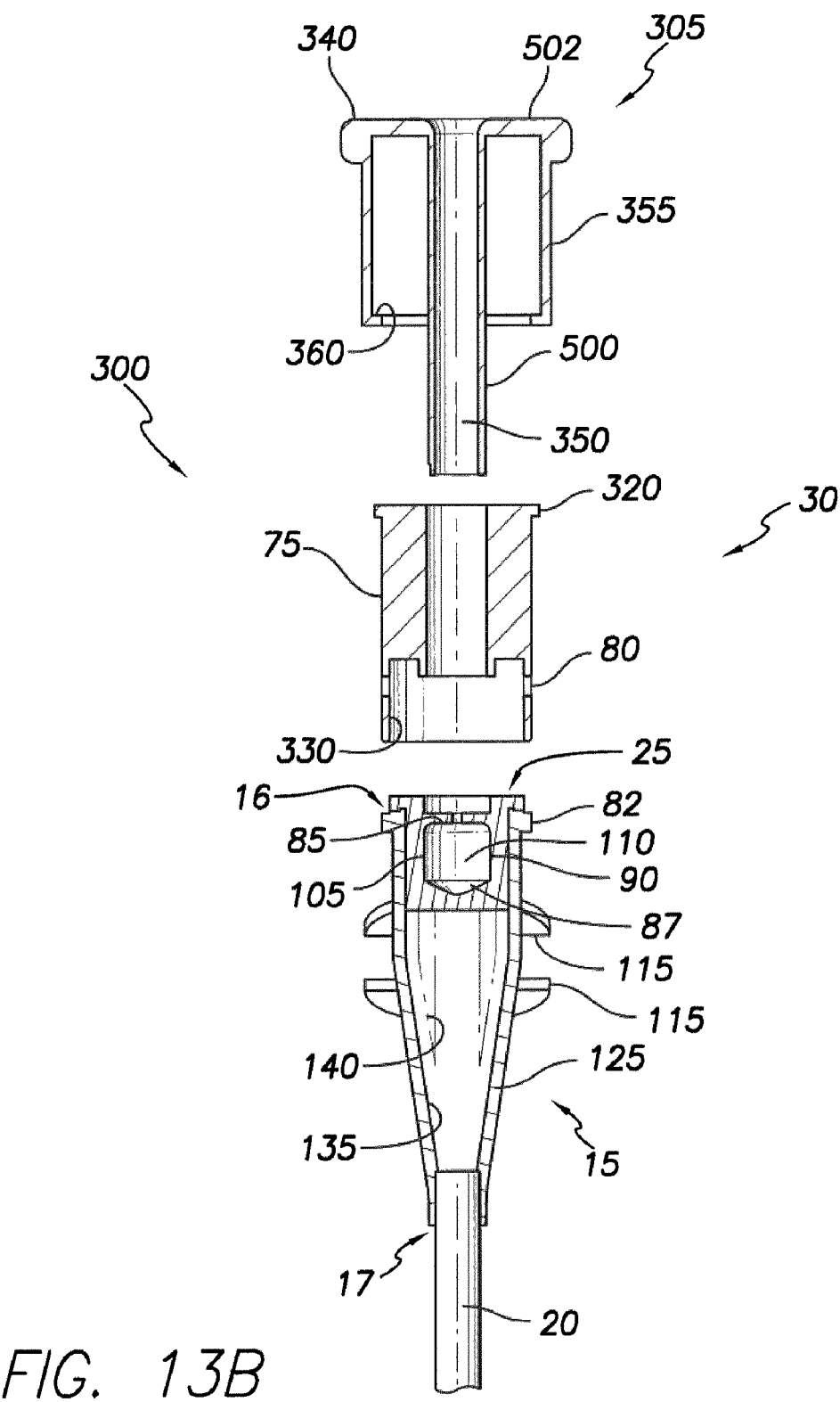
FIG. 13B is a cross-sectional elevation of the assembly as taken along section line D-D of FIG. 13A.
Figure 13C:
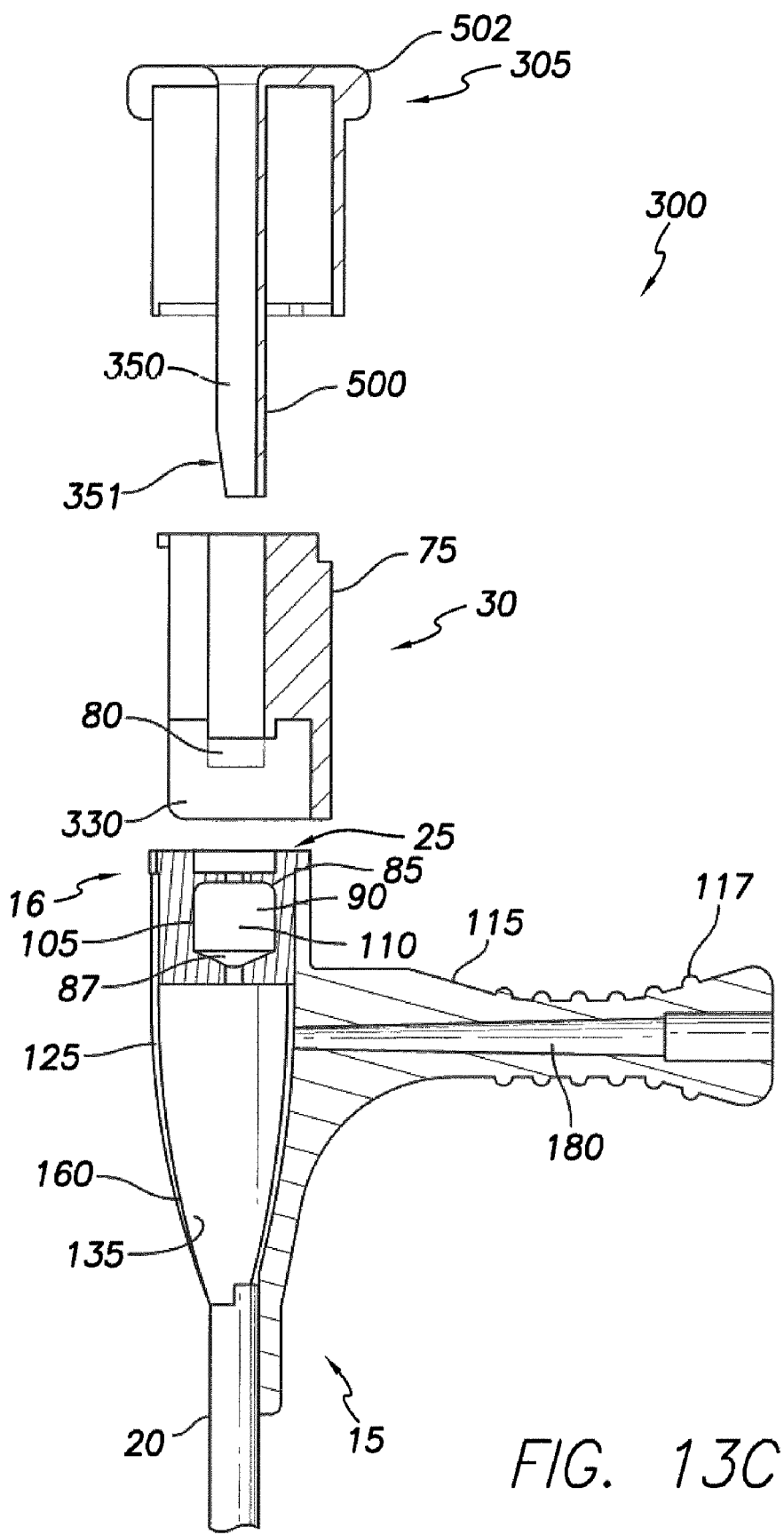
FIG. 13C is a cross-sectional elevation of the assembly as taken along section line E-E of FIG. 13A.
Figure 14A:
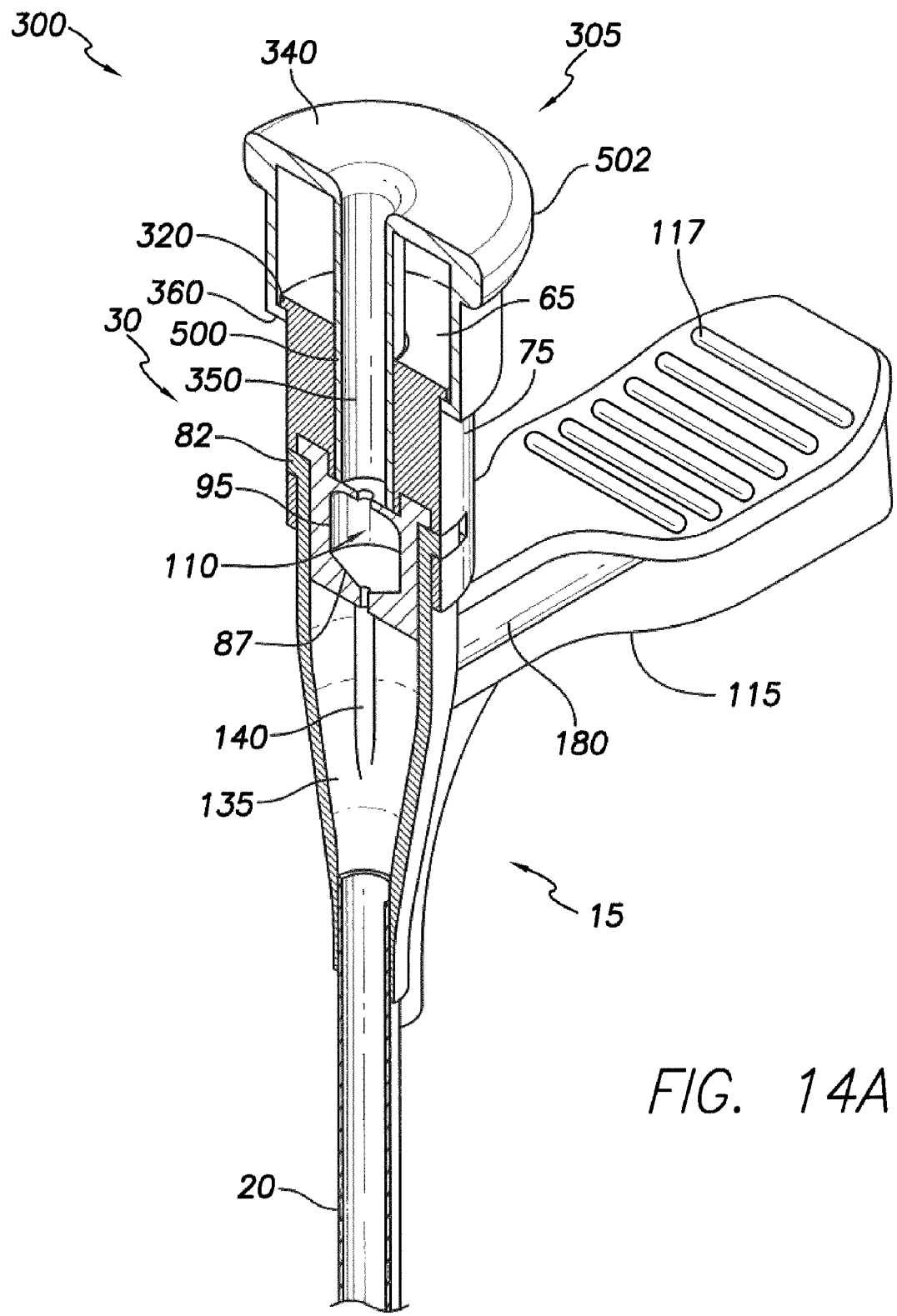
FIG. 14A is an isometric cross-sectional elevation of the assembly as taken along section line D-D of FIG. 13A, except the assembly is shown assembled and in a disengaged state.
Figure 14B:
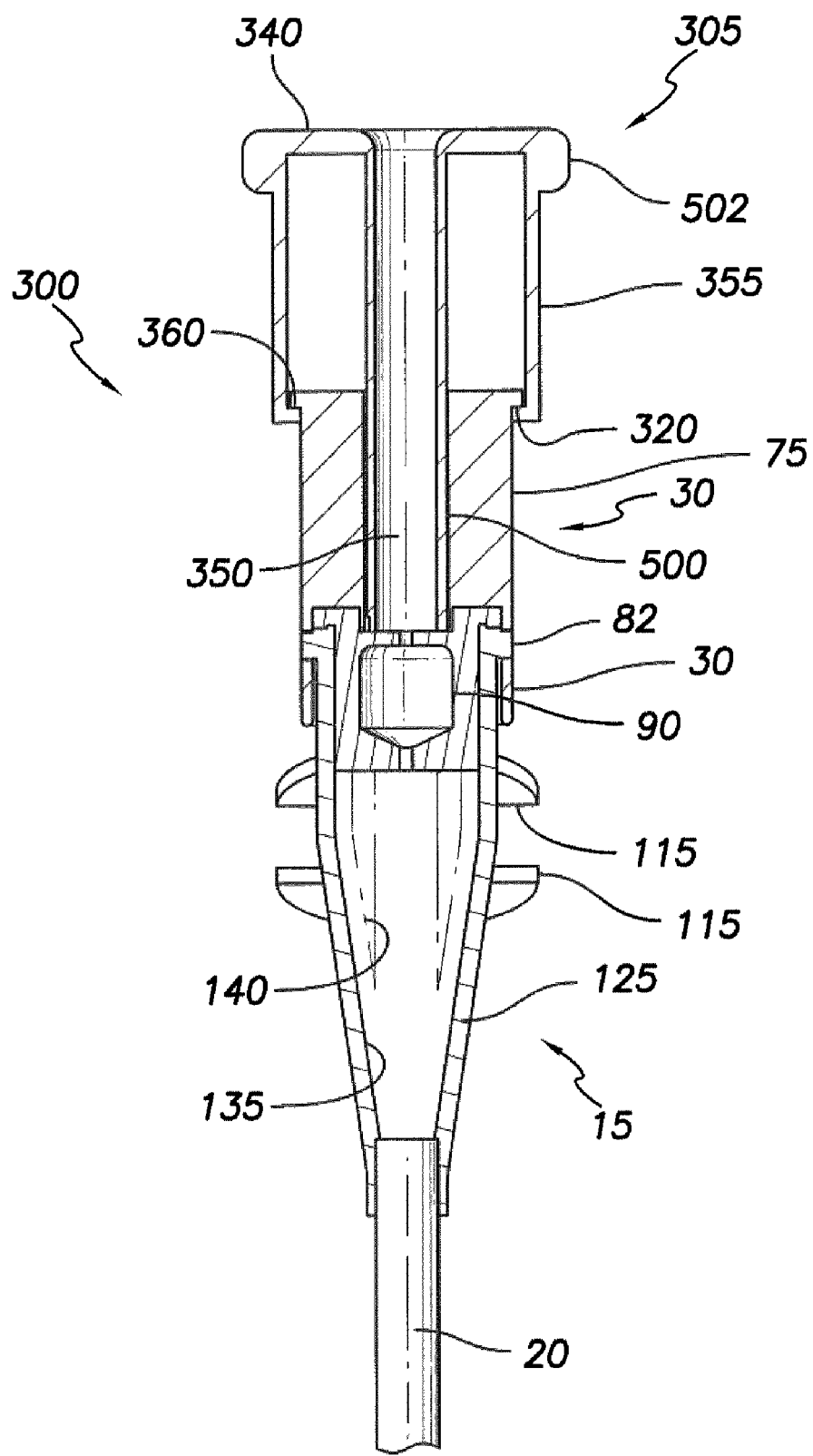
FIG. 14B is the same view as FIG. 13B, except the assembly is shown assembled and in a disengaged state.
Figure 14C:
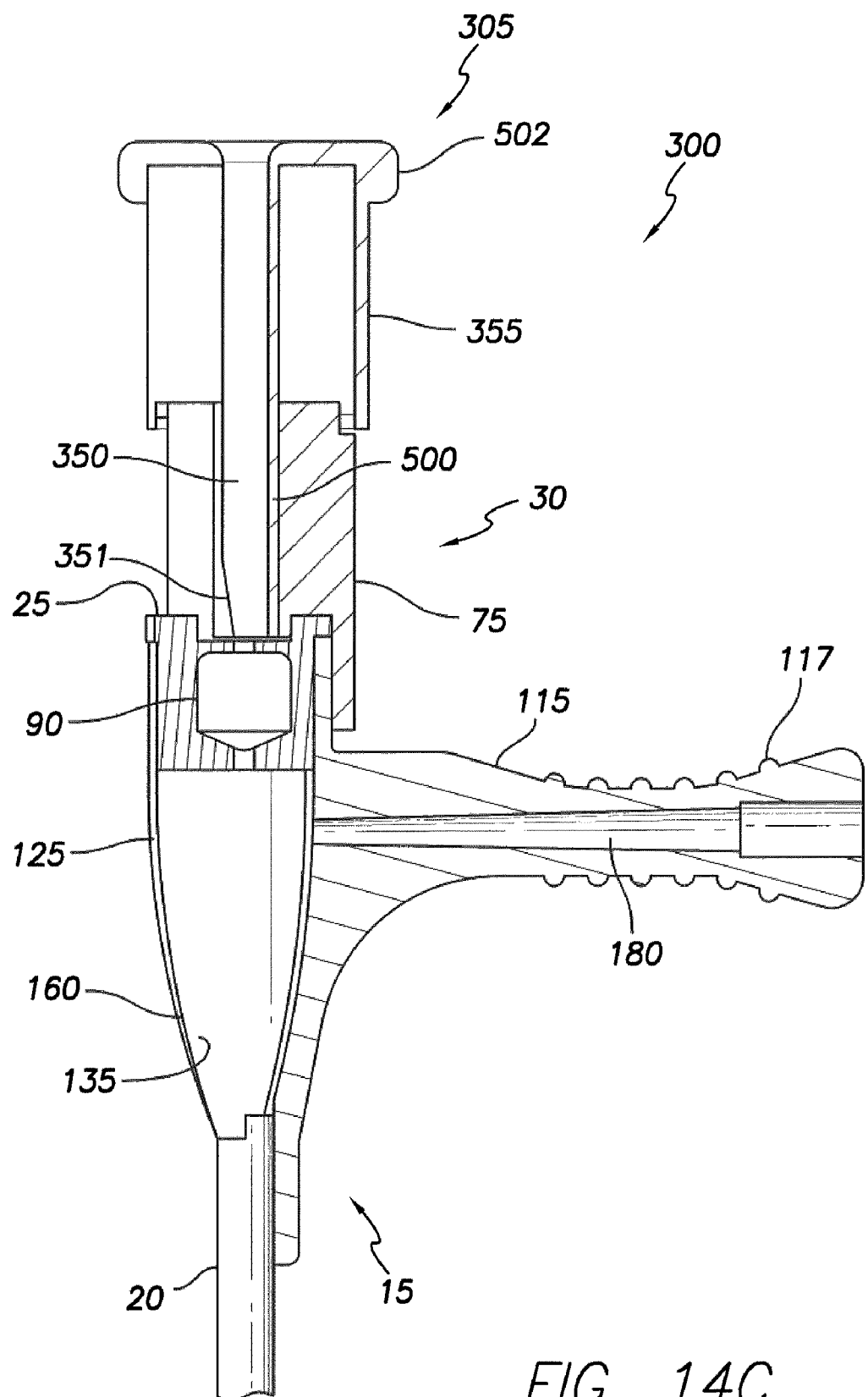
FIG. 14C is the same view as FIG. 13C, except the assembly is shown assembled and in a disengaged state.
Figure 15A:
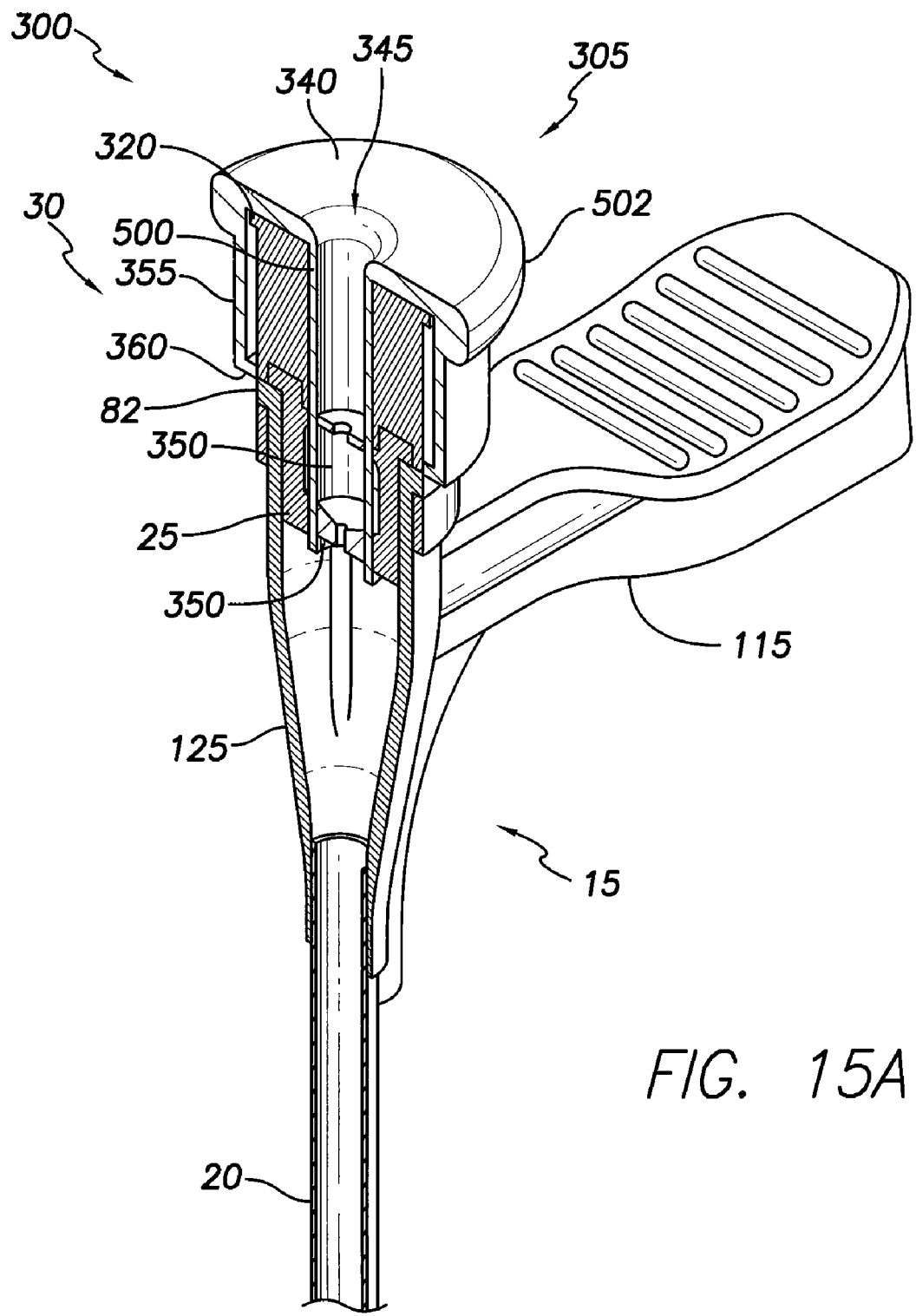
FIG. 15A is the same view as FIG. 14A, except the assembly is shown in an engaged state.
Figure 15B:
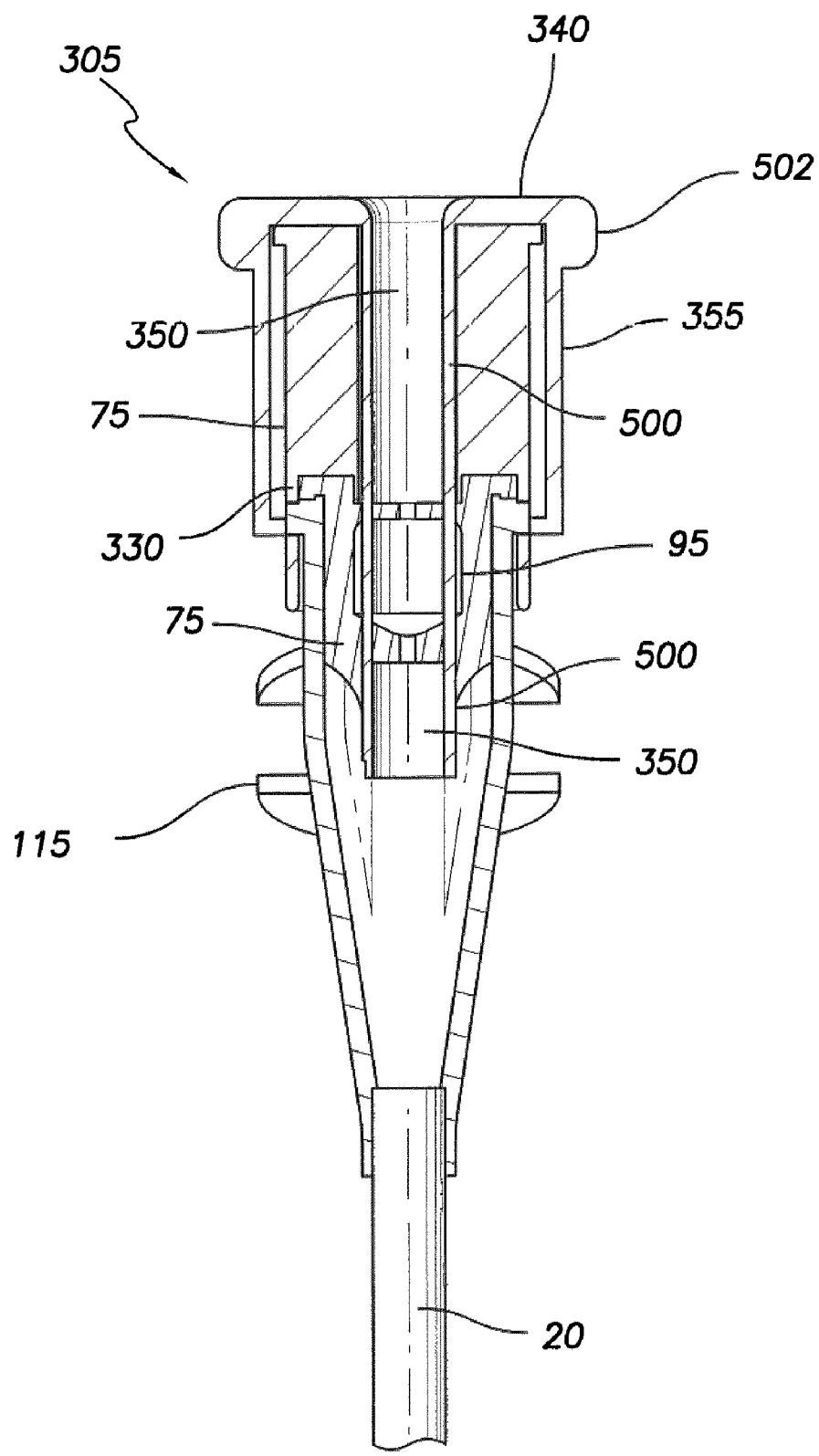
FIG. 15B is the same view as FIG. 14B, except the assembly is shown in an engaged state.
Figure 15C:
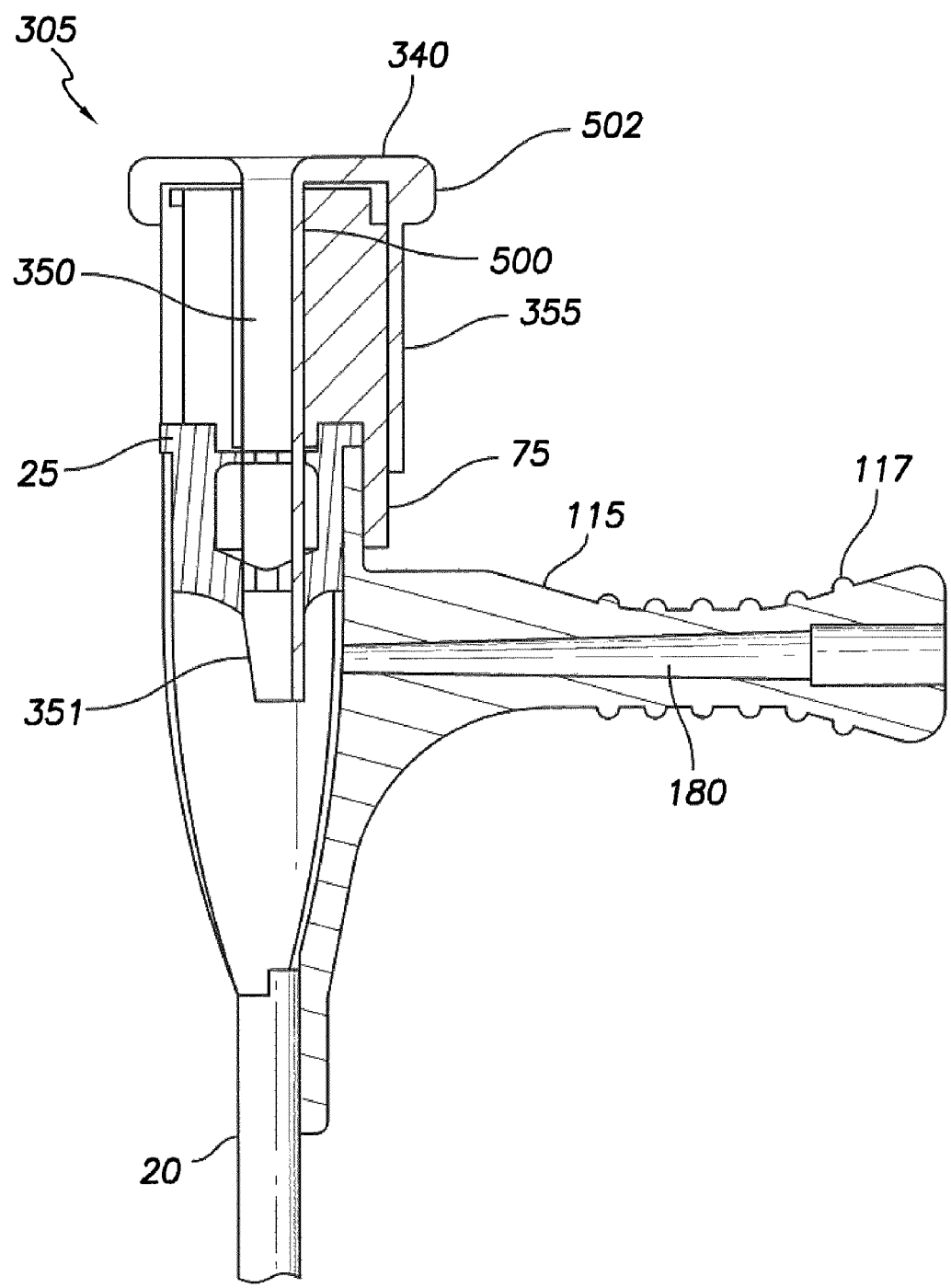
FIG. 15C is the same view as FIG. 14C, except the assembly is shown in an engaged state.

For a detailed discussion of the components of the slittable delivery device assembly 300, reference is now made to FIGS. 9-15C, in which like reference numbers are used for elements similar to the elements described above with reference to the slittable delivery device 10. FIG. 9 is an embodiment of a slittable delivery device assembly 300 including the slittable delivery device of FIG. 1. FIGS. 10A-10C are exploded isometric and cross-sectional views, respectively, of another embodiment of the slittable delivery device assembly 300 of FIG. 9. FIGS. 11A-11C are the same views of the assembly 300 as in FIGS. 10A-10C, except the assembly 300 is shown assembled and in a disengaged or non-valve bypass state, wherein the valve bypass tool has not forced open the hemostasis valve. FIGS. 12A-12C are the same views of the assembly 300 as in FIGS. 11A-11C, except the assembly 300 is shown assembled and in an engaged or valve bypass state, wherein the valve bypass tool has forced open the hemostasis valve. FIGS. 13A-13C are exploded isometric and cross-sectional views, respectively, of still another embodiment of the slittable delivery device assembly 300 of FIG. 9. FIGS. 14A-14C are the same views of the assembly 300 as in FIGS. 13A-13C, except the assembly 300 is shown assembled and in a disengaged or non-valve bypass state, wherein the valve bypass tool has not forced open the hemostasis valve. FIGS. 15A-15C are the same views of the assembly 300 as in FIGS. 14A-14C, except the assembly 300 is shown assembled and in an engaged or valve bypass state, wherein the valve bypass tool has forced open the hemostasis valve.

As can be understood from FIGS. 9-15C, the slittable delivery device assembly 300 may include a slittable delivery device 10 and a bypass assembly 302. The slittable delivery device assembly 300 may include a hub 15, a sheath 20, an integrated hemostasis valve 25, a cap 30, a handle 115 and a valve bypass tool 305. The components of the hub 15, sheath 20, integrated hemostasis valve 25 and handle 115 are generally similar to and generally operate similar to the like numbered elements as discussed above with respect to FIGS. 1-8B.

The bypass assembly 302 may include a cap 30 and a valve bypass tool 305. In some embodiments, the cap 30 is generally similar to and operates generally similar to the cap 30 as described above. That is, the cap 30 of the bypass assembly 302 includes a proximal face 65, a lateral generally cylindrical wall 75, and tab receiving openings 80 in the wall 75. The cap 30 of the bypass assembly 302 is configured to generally receive the hub 15, and thereby partially enclose the proximal face of the valve 25 and maintain the valve 25 within the hub 15 to create a fluid tight seal. The tab receiving openings 80 receive tabs 82 (on the hub 15), thereby maintaining the cap 30 in position with respect to the hub 15. As discussed in more detail below, the cap 30 of the bypass assembly 302 may also be configured to maintain the valve bypass tool 305 in position when the valve bypass assembly 302 is in an engaged or disengaged state In some embodiments, as shown in FIGS. 10A-15C, the proximal face 65 of the cap 30 also includes the U-shaped opening 70 as described above with respect to FIGS. 1-8B. In some embodiments, as shown in FIG. 9, the proximal face 65 of the cap 30 includes a generally V-shaped opening 315. The V-shaped opening 315 operates similar to the U-shaped opening 70 and is similarly configured to receive a distal end of the cardiac surgical device 5 and similarly provides access to a portion of the valve 25 such that the valve may be slit during removal of the assembly 300. In addition, the openings 70, 315 are configured to receive at least a portion of the shaft 500 of the valve bypass tool 305 when the assembly 302 is assembled.

In some embodiments, as shown in FIGS. 13A-15C, the proximal face 65 of the cap 30 may include a beveled edge 320. As discussed in more detail below with reference to FIGS. 14A-14C, the cap 30 may be configured to be received in the valve bypass tool 305 and the beveled edge 320 may help to maintain the bypass assembly 302 in an assembled state.

In some embodiments, as shown in FIGS. 10A-15C, the lateral generally extending cylindrical wall 75 of the cap 30 includes an outer surface 333 and an inner surface 331. The outer surface 333 of the wall 75 includes a longitudinally extending opening or slot 326 and an arcuate opening 325. The slot 326 intersects the proximal face 65 of the cap 30 at the open end of the U of the U-shaped opening 70 to merge with the U-shaped opening 70. The arcuate opening 325 intersects at the distal end of the slot 326 and generally corresponds to a hub receiving groove 330 on the distal end of the inner surface 331 of the wall 75. In some embodiments, as shown in FIG. 9, the lateral generally cylindrical wall 75 includes a wide longitudinally extending opening or slot 327 that intersects the proximal face 65 of the cap 30 at the open end of the V-shaped opening 315 to merge with the V-shaped opening 315 and generally extends the length of the wall 72. Similar to the arcuate opening 77 discussed above, the openings 325, 326, 327 are configured to expose a proximal portion of the hub 15 and the shaft 20, and the valve 25. More specifically, the openings 325, 326, 327 expose a portion of the slittable valve 25 and the slit path or strip 23 extending the length of the hub 15, thereby allowing the tool blade 50 to access the slit strip 23 and the slittable valve 25.

In some embodiments, the inner surface 331 of the lateral generally cylindrical wall 75 includes a hub receiving groove 330 at a distal end of the wall 75 and a locking groove 335 at a proximal end of the wall 75. As indicated in FIGS. 9-12C, the locking groove 335 is configured to receive a tab 310 on the valve bypass tool 305. As shown in FIGS. 9-15C, the hub receiving groove 330 is configured to receive the hub 15.

Figure 10A:
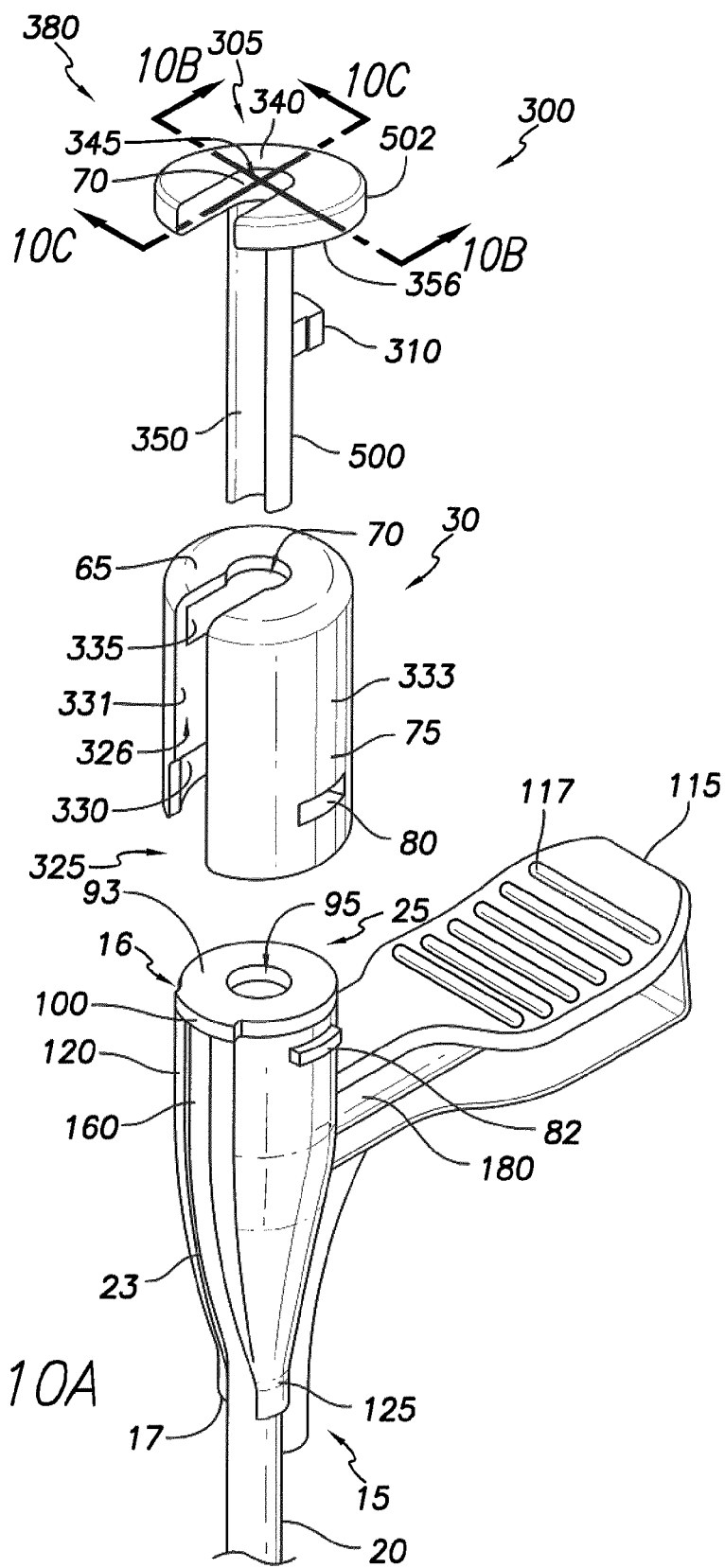
FIG. 10A is an exploded isometric view of another embodiment of the slittable delivery device assembly of FIG. 9.
Figure 10B:
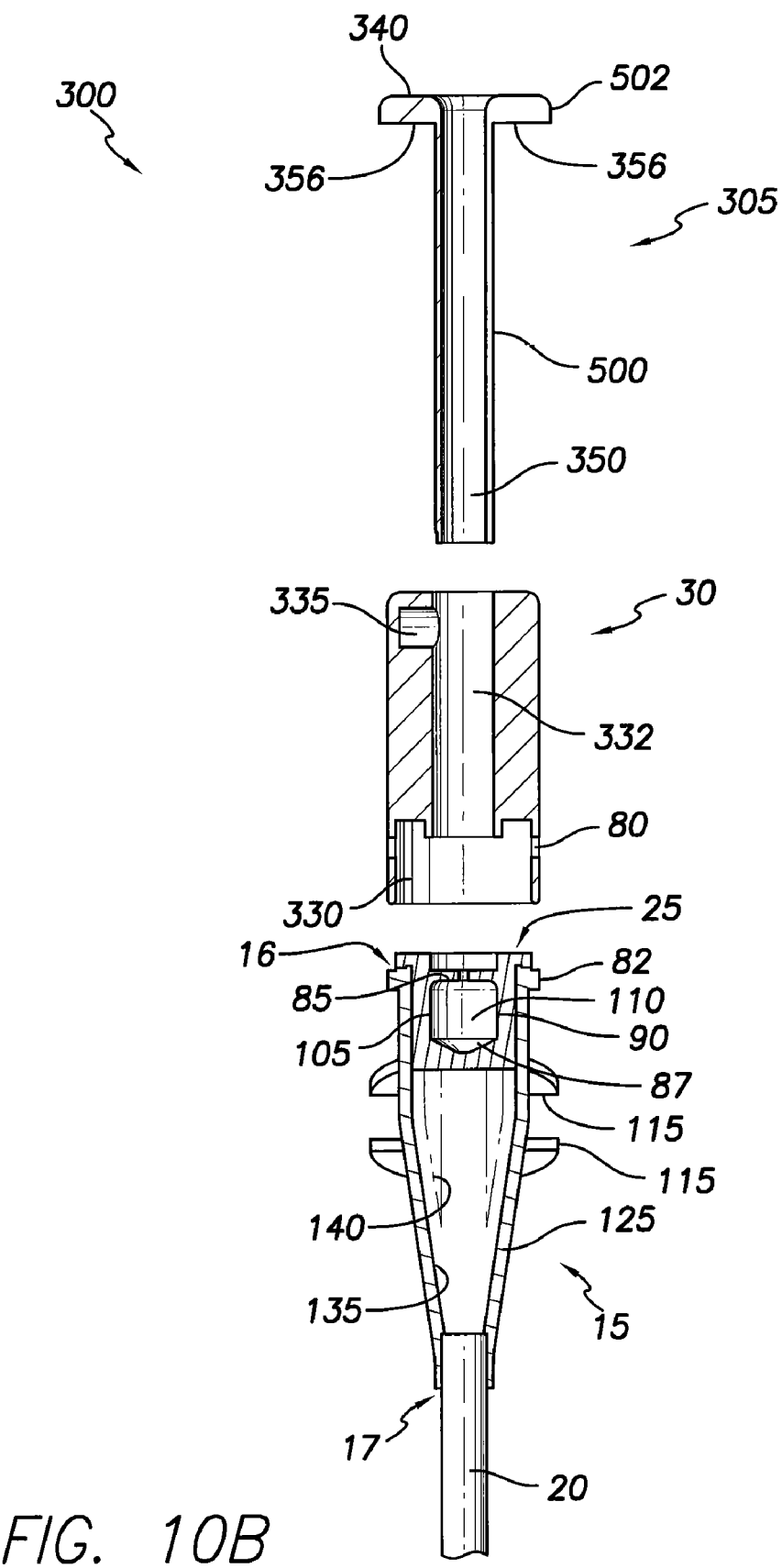
FIG. 10B is a cross-sectional elevation of the assembly as taken along section line B-B of FIG. 10A.
Figure 10C:
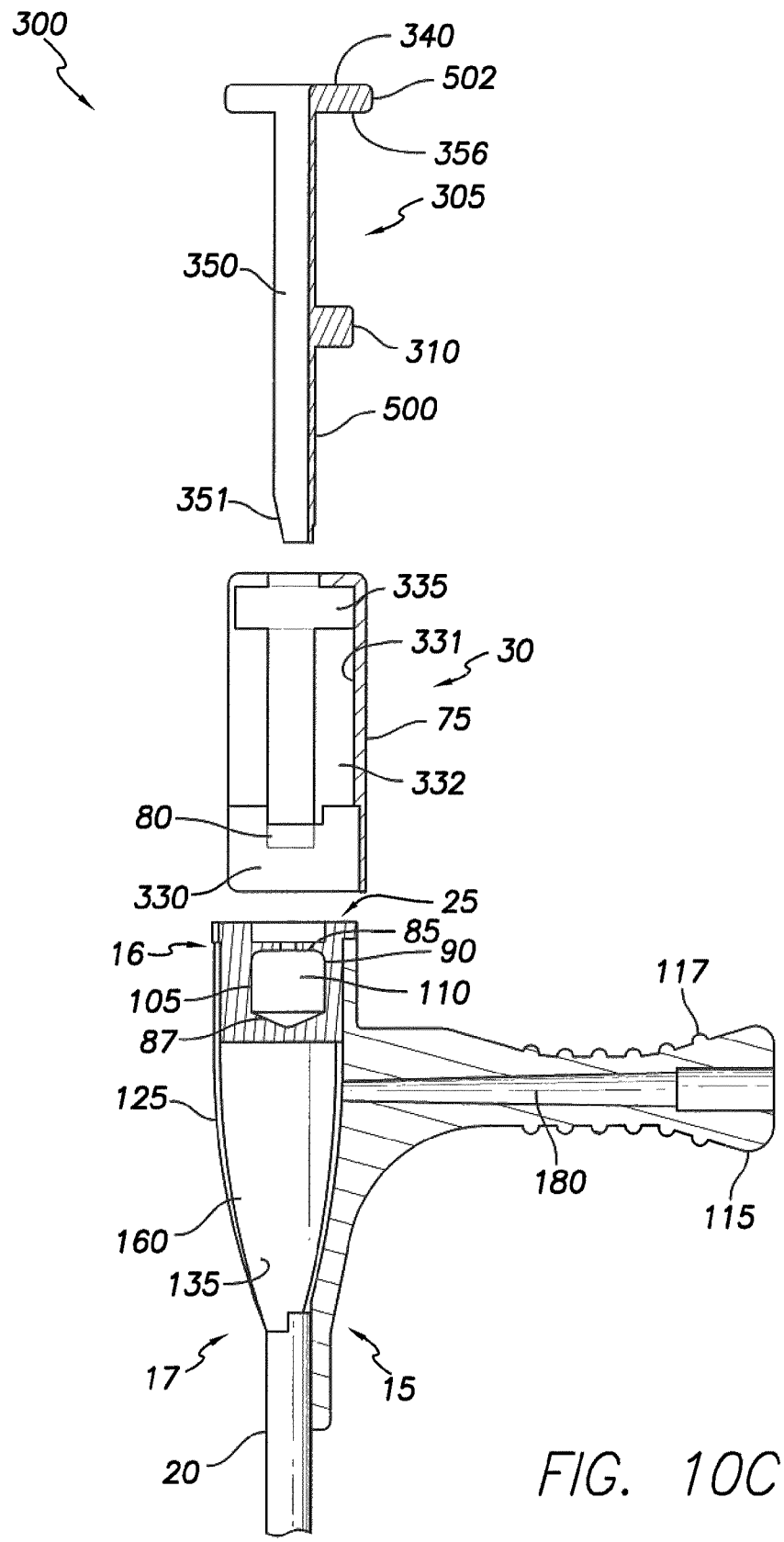
FIG. 10C is a cross-sectional elevation of the assembly as taken along section line C-C of FIG. 10A.
Figure 11A:
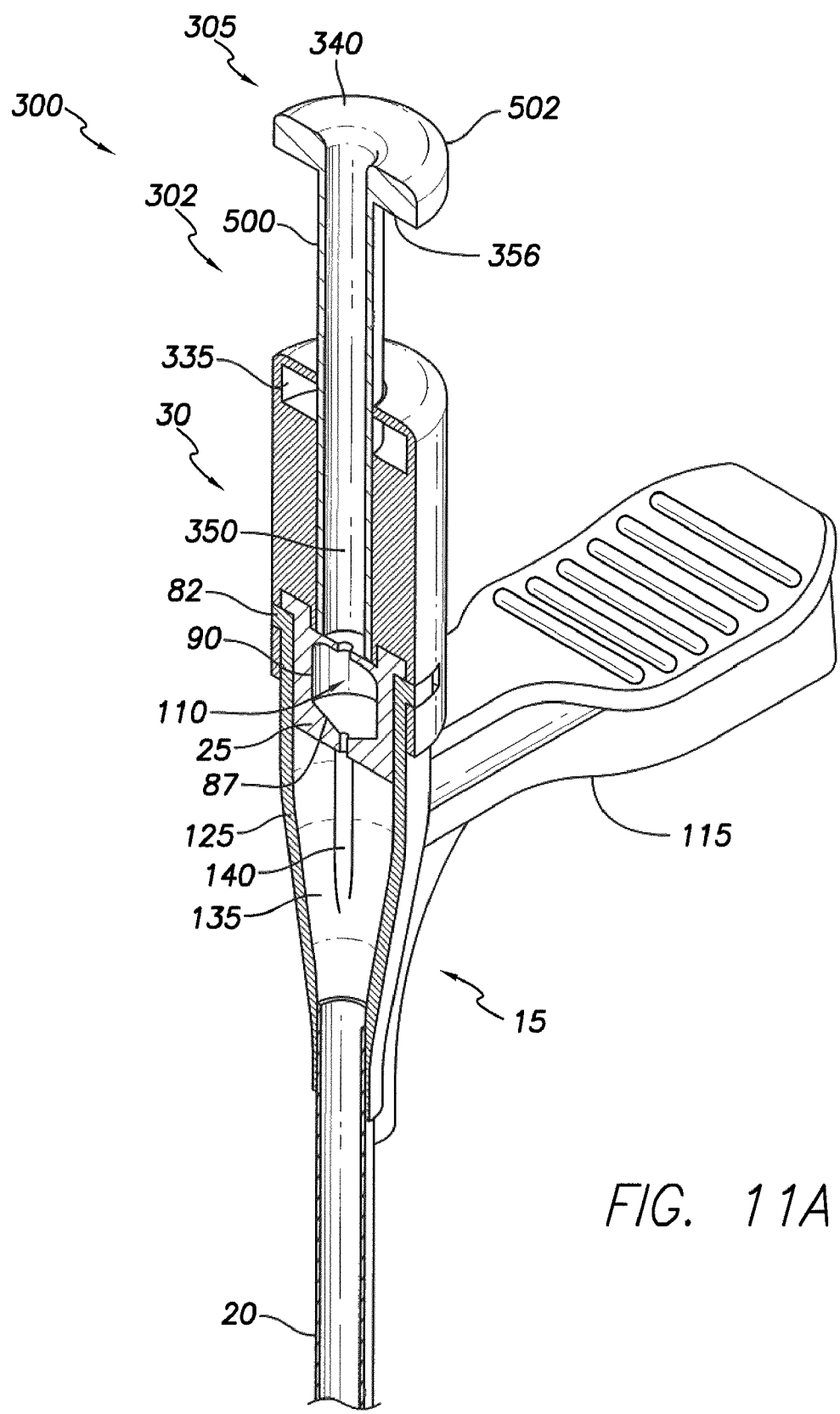
FIG. 11A is an isometric cross-sectional elevation of the assembly as taken along section line B-B of FIG. 10A, except the assembly is shown assembled and in a disengaged state.
Figure 11B:
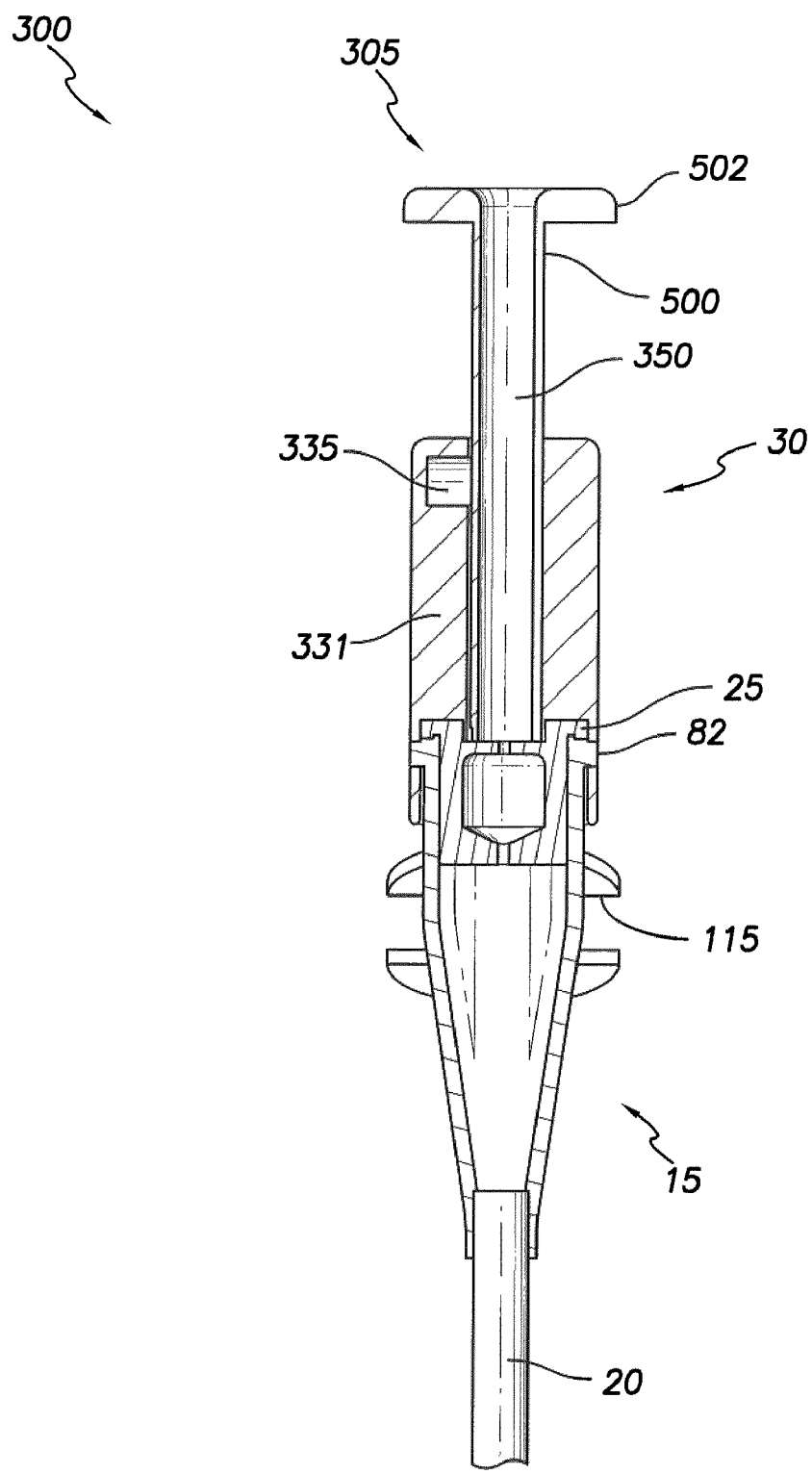
FIG. 11B is the same view as FIG. 10B, except the assembly is shown assembled and in a disengaged state.
Figure 11C:
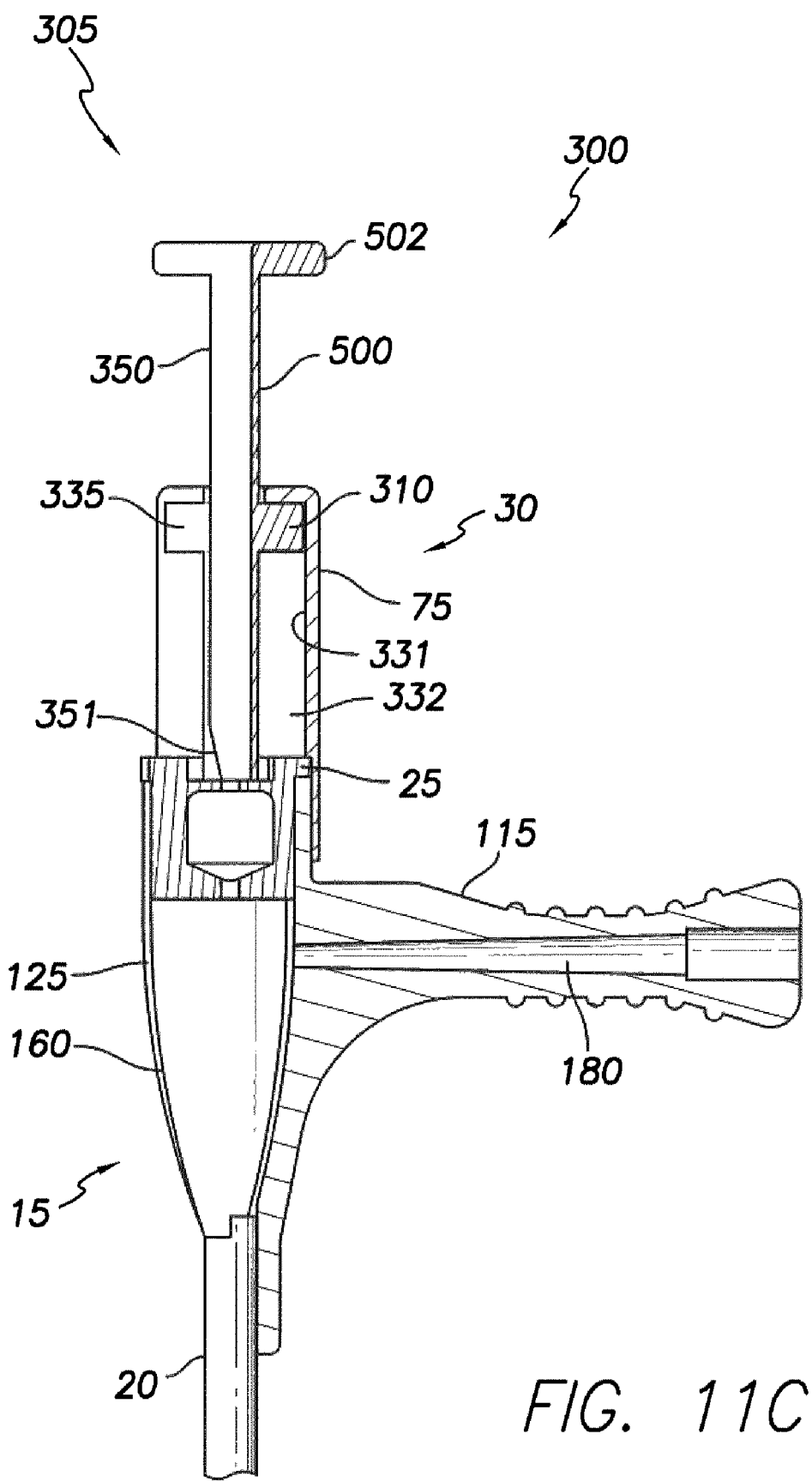
FIG. 11C is the same view as FIG. 10C, except the assembly is shown assembled and in a disengaged state.
Figure 12A:
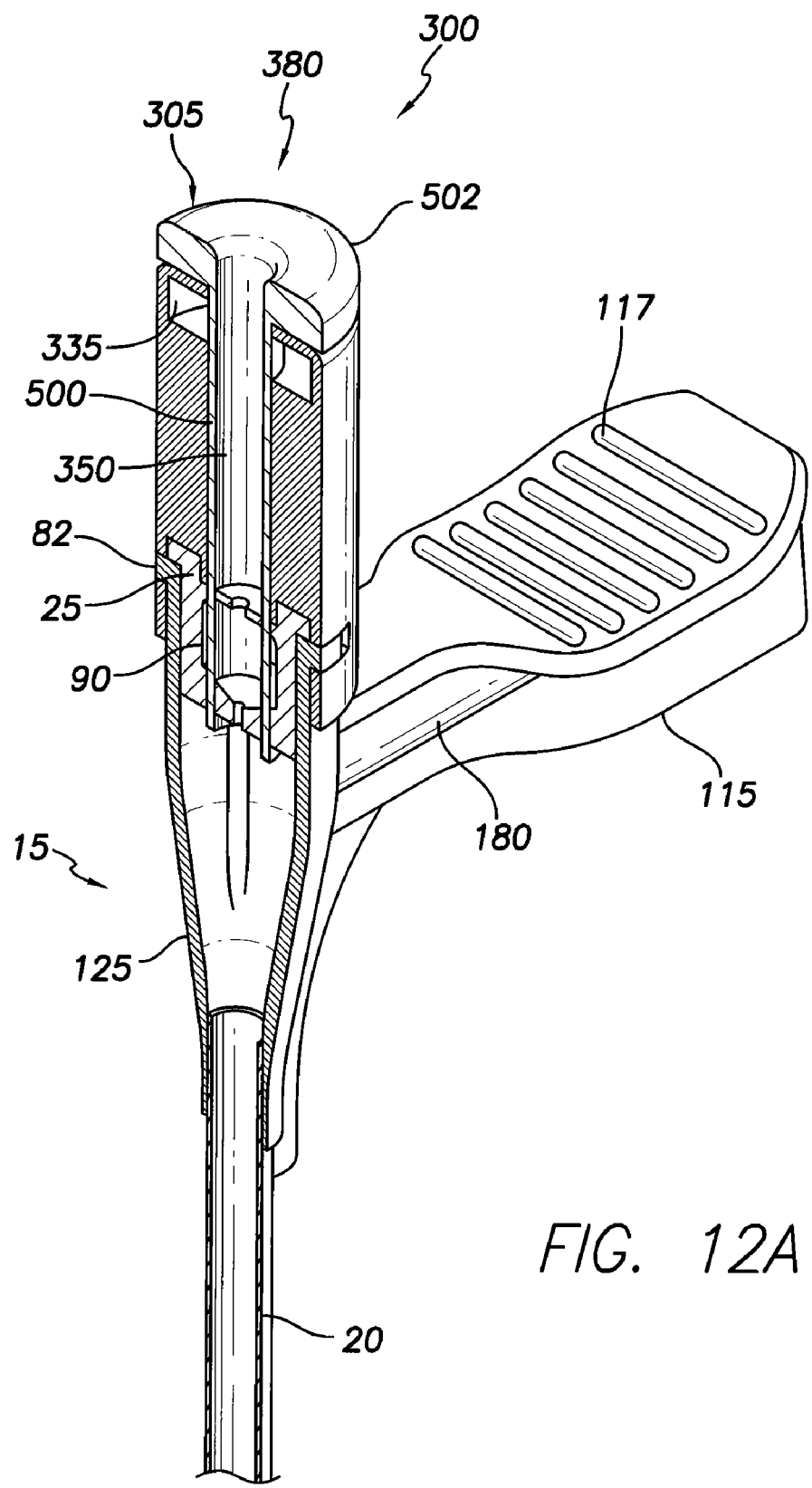
FIG. 12A is the same view as FIG. 11A, except the assembly is shown in an engaged state.
Figure 12B:
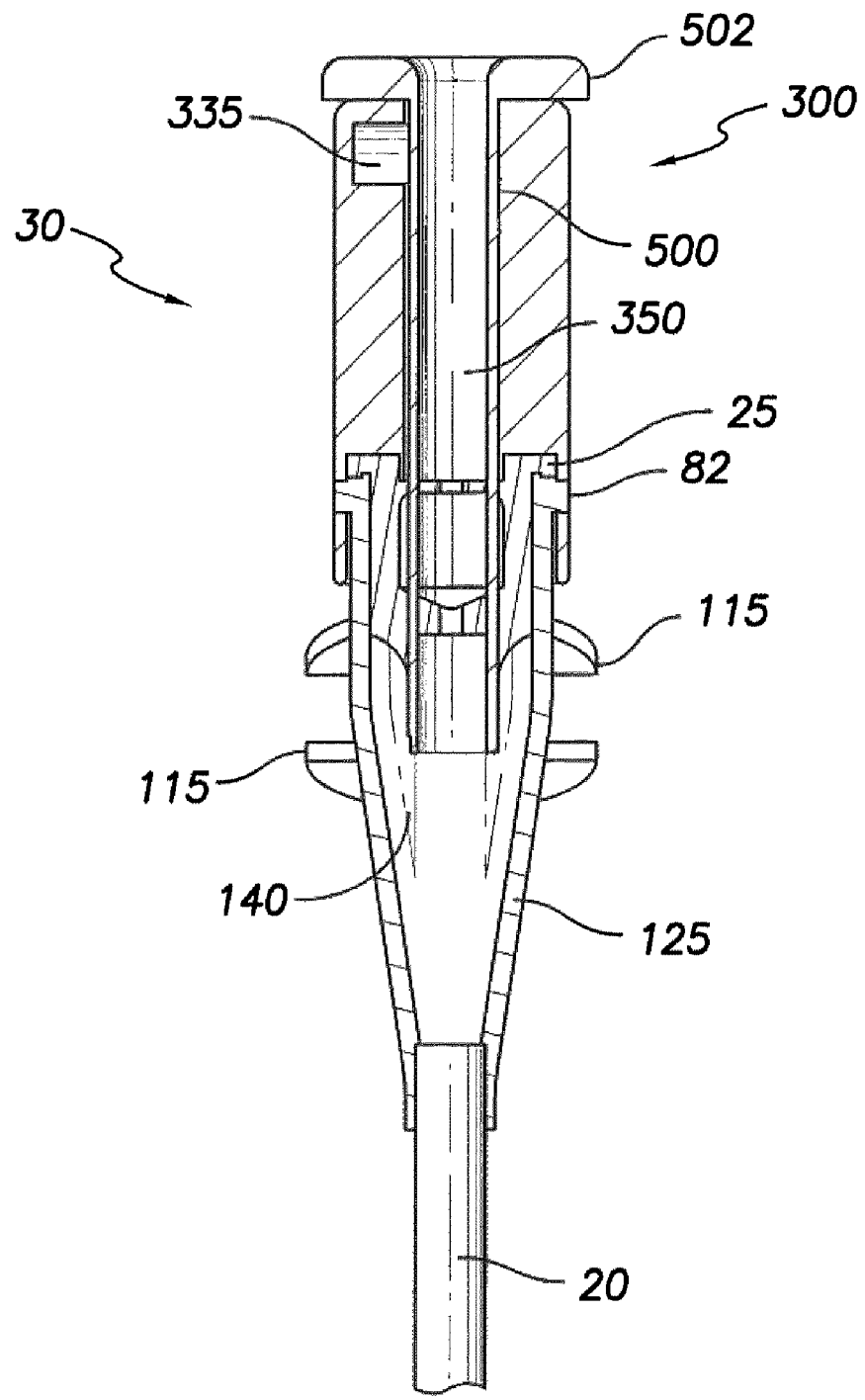
FIG. 12B is the same view as FIG. 11B, except the assembly is shown in an engaged state.
Figure 12C:
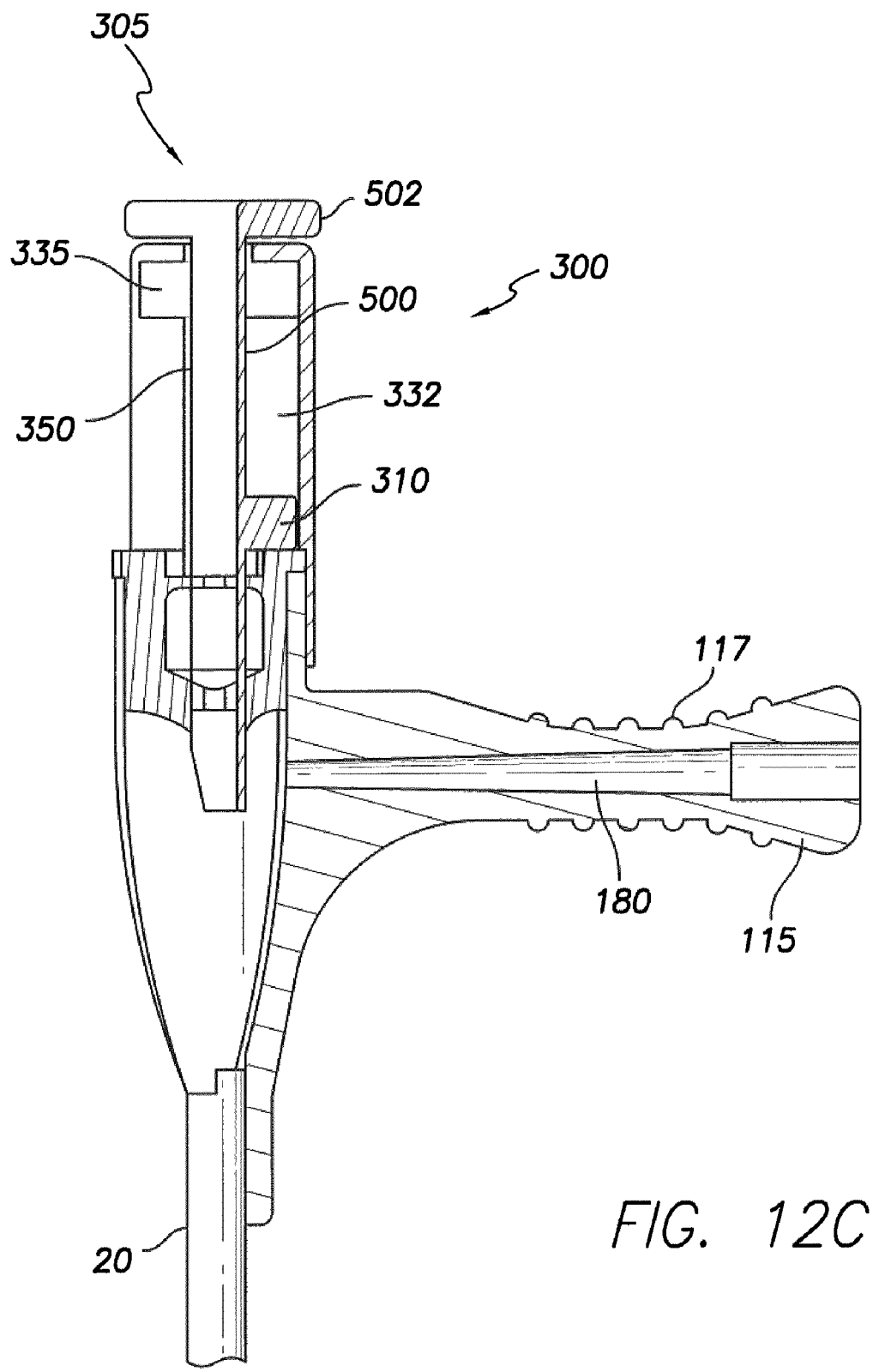
FIG. 12C is the same view as FIG. 11C, except the assembly is shown in an engaged state.

As can be understood from FIGS. 10C, 11C and 12C, the inner surface 331 of the wall 75, the hub receiving groove 330 and the locking groove 335 may define the boundaries of a tab receiving channel 332. As discussed in more detail below, when the tab 310 of the valve bypass tool 305 engages the locking groove 335, the bypass assembly 302 will be maintained in a disengaged state, where the longitudinal movement of the valve bypass tool 305 in a distal direction is hindered. To transition to the engaged state, the tab 310 may be rotated into the channel 332, and the bypass tool 305 may displaced distally so the tapered end 351 of the bypass tool 305 passes through the valve 25, thereby moving the bypass assembly 302 from a disengaged to an engaged state.

As can be understood from FIGS. 9-15C and 17, the valve bypass tool 305 may include a head 502 and a shaft 500 extending proximally fro the head 502. The head 502 may be disk shaped and have a circular, rectangular or other shape. The head 502 may include a proximal face 340, a distal face 356, a U-shape or V-shape opening 345. The shaft 500 may include an open channel 350 defined in and longitudinally extending along the shaft 500.

As can be understood from FIGS. 9-15C, in some embodiments, the valve bypass tool 305 and the cap 30 may form an integrated bypass assembly 302, which may be coupled to the hub 15 of the slittable delivery device 10 to form an integrated device 300. Where the valve bypass tool 305 is part of the integrated bypass assembly 302, the valve bypass tool 305 may be slidingly coupled to the cap 30 to create the integrated bypass assembly 302. Where the bypass assembly 302 is part of the integrated assembly 300, the bypass assembly 302 may be operably coupled to the hub 15 of the slittable delivery device 10 via the hub tabs 82.

Figure 17:
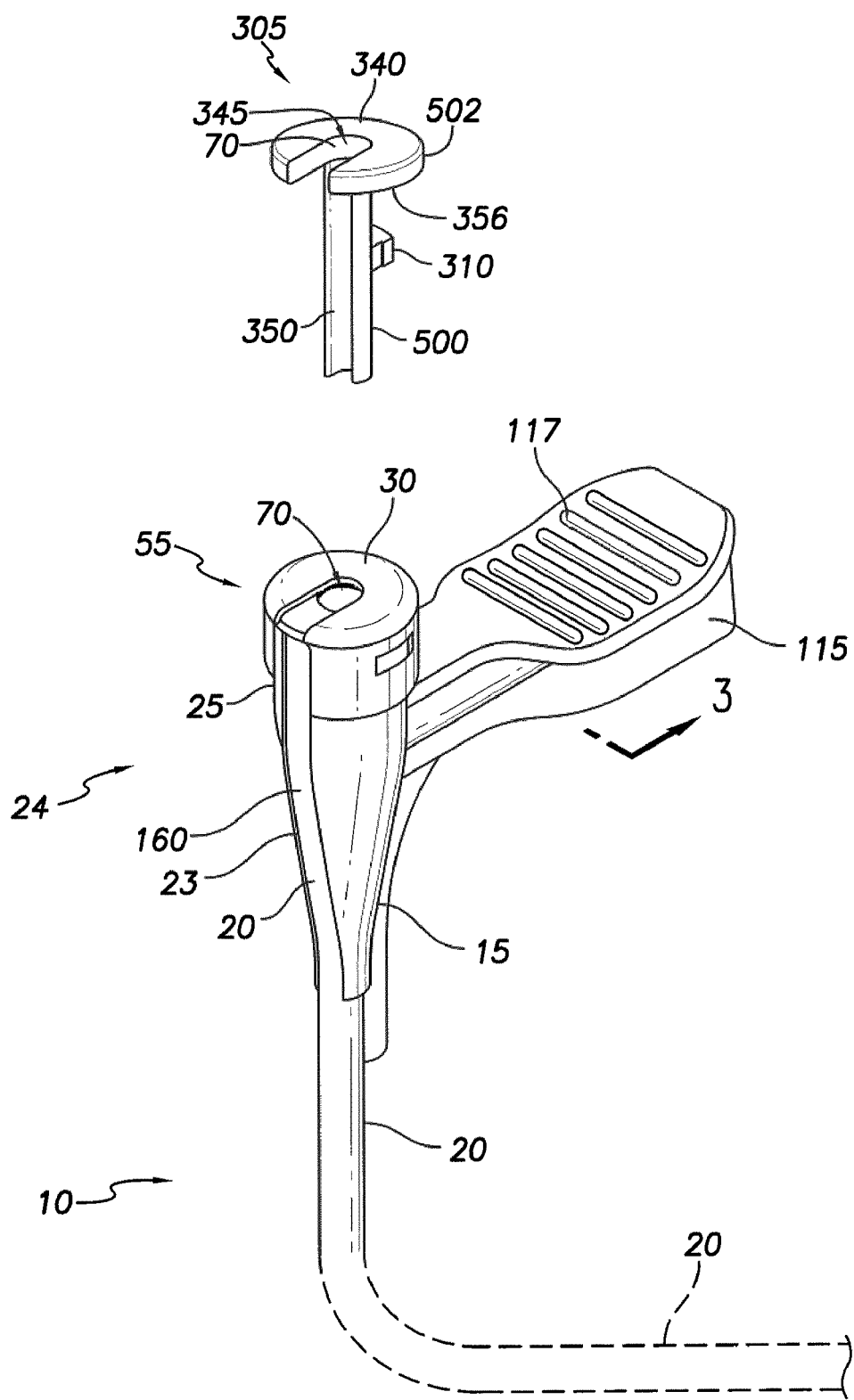
FIG. 17 is an embodiment of a slittable delivery device assembly comprising the slittable delivery device of FIG. 2 and an independent valve bypass tool.
Figure 18:
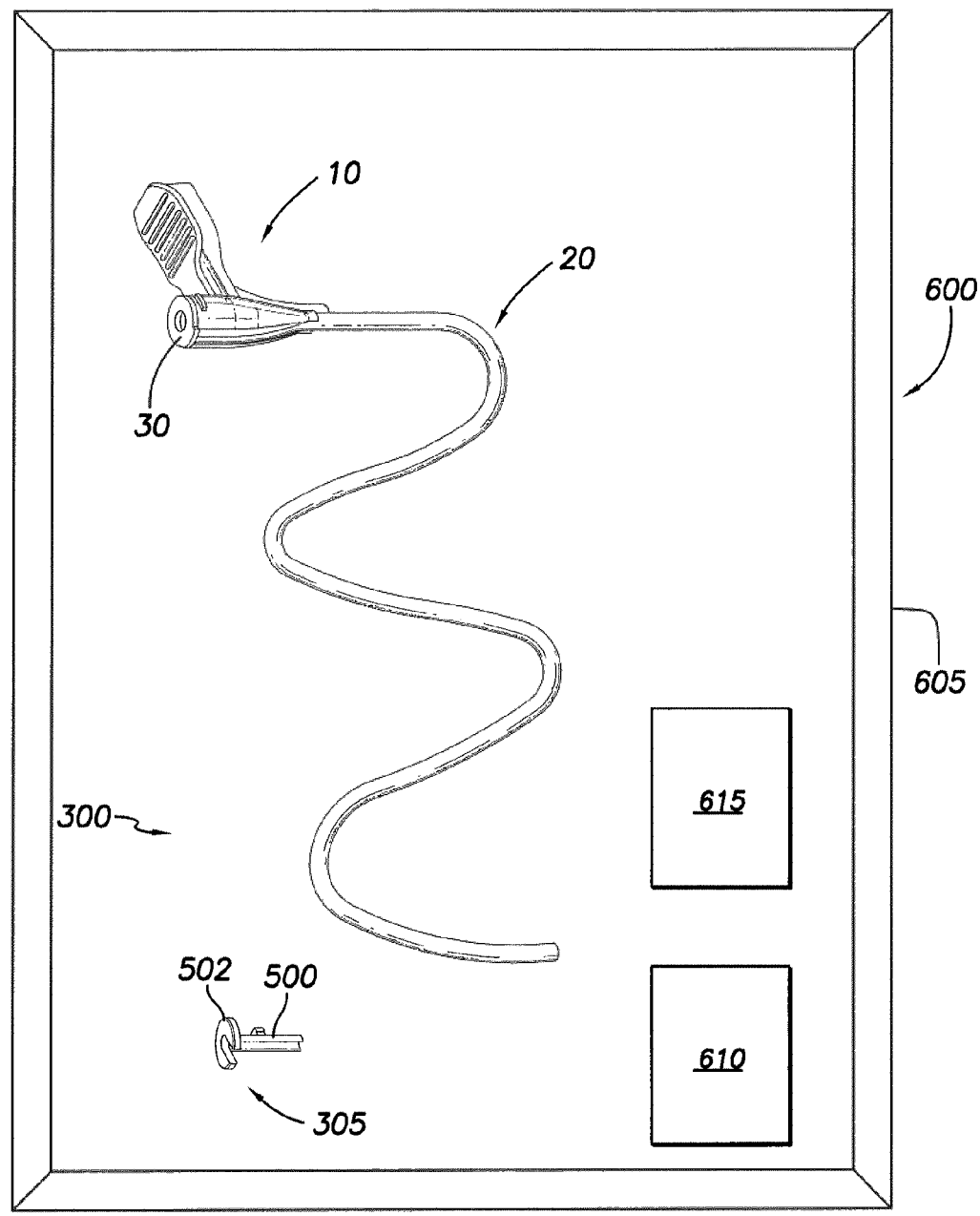
FIG. 18 is a kit comprising the slittable delivery device assembly and independent valve bypass tool of FIG. 17.

As can be understood from FIG. 17, in some embodiments, the cap 30 may be coupled to the hub 15 of the slittable delivery device 10 as part of the slittable delivery device 10, and the valve bypass tool 305 may be a separate tool 305 from the slittable delivery device 10. In such an embodiment, the separate valve bypass tool 305 may be inserted into and removed from the hemostasis valve of the slittable delivery device 10 as needed, even being capable of being reused with the slittable delivery device 10 or another slittable delivery device 10 until the lead 5 is implanted as desired.

The valve bypass tool 305 enables a user to insert and maneuver variously sized surgical devices 5 through the valve 25 without the use or requirement of a secondary insertion tool, such as a peelable non-integrated valve bypass tool, a slittable non-integrated valve bypass tool, an integrated valve bypass tool that is removable, or other types of non-integrated valve bypass tools known in the art. The valve bypass tool 305 may be made of acrylonitrile butadiene styrene ("ABS"), polycarbonate, nylon, high density polyethylene ("HDPE"), or etc.

The proximal face 340 of the valve bypass tool 305 may be generally circular and includes the U-shaped (see FIGS. 10A and 13A) or V-shaped opening (see FIG. 9) 345. The opening 345 is configured to receive the distal end of the cardiac surgical device 5.

The open channel 350 in the shaft 500 of the valve bypass tool 305 intersects the proximal face 340 of the tool 305 at the closed end of the U-shaped or V-shaped opening 345 to merge with the opening 345. The tool 305 is configured to be received in the cap opening 70 such that the opening 345 and open channel 350 are aligned with the opening 70 and opening 326, respectively. The bypass assembly 302 is mounted on the hub 15 with the openings 70, 315, 345, 350 so aligned with each other and with the slitting strip 23 in the hub 15, the assembly 302 being maintained on the hub 15 via the mating of the tabs 82 of the cap 30 in the slots 80 of the hub 15.

The aligned openings 70, 315, 345, 350 allow access to the slittable delivery device 10 and in some embodiments, may expose a portion of the valve 25 such that valve may be slit. The aligned openings 70, 315, 345, 350 also allow the valve bypass tool 305 and cap 30 (e.g., the bypass assembly 302) to be removed from about the surgical device 5 during or after slitting of the delivery device 10.

As shown in FIGS. 10C, 11C and 13C, a distal end 351 of the shaft 500 may be tapered. As discussed in more detail below, the tapered end 351 of the shaft 500 engages the valve 25 such that the shaft 500 maintains the valve 25 in an open state when the bypass assembly 302 is in an engaged state. Friction between the valve 25 and the shaft 500 extending through the valve 25 maintains the shaft 500 within the valve 25, thereby keeping the valve open.

In some embodiments, as shown in FIGS. 10A, 10C, 12A and 12C, the valve bypass tool 305 may also include a tab 310 on the outer surface of the shaft 500. As can be understood from FIG. 11C, the tab 310 may be configured to be received in the locking groove 335 to prevent longitudinal displacement of the tool 305 in a distal direction from a disengaged state towards an engaged or bypass state. The tab 310 passes along the channel 332 when the tool 305 travels between the engaged and disengaged states, the channel 332 and tab 310 interacting to prevent rotational movement of the valve bypass tool 305 when the tab 310 is not located adjacent to the locking groove 335. As can be understood from FIG. 12C, in an engaged state, the tab 310 may abut the valve 25, thereby hindering further distal movement of the valve bypass tool 305.

As indicated in FIGS. 13A-15C, in some embodiments, the valve bypass tool 305 may also include a generally laterally extending cylindrical wall 355 and an edge receiving lip 360. The wall 355 extends from its proximal end at the cap side 356 of the proximal face 340 of the bypass tool 305 to its distal end which includes an edge receiving lip 360. The edge receiving lip 360 is configured to receive the beveled edge 320 of the proximal face 65 of the cap 30, thereby preventing the tool 305 from being proximally removed off of the cap 30.

In use, the slittable delivery device 10 is coupled to the bypass assembly 302 including an integrated valve bypass tool 305, which maintains the valve 25 in an open position when the assembly 300 is in an engaged or bypass state (see FIGS. 12A-12C and 15A-15C), thereby allowing the insertion of surgical devices 5 without the need for a secondary insertion tool. In turn, when in disengaged or non-bypass state (see FIGS. 11A-11C and 14A-14C), the integrated valve bypass tool 305 will allow the valve 25 to remain in a closed position. The bypass assembly 302 is also configured via its slotted configuration such that when it is coupled to the slittable delivery device 10, the bypass assembly 302 will not hinder the accessibility of the slit path of the delivery device 10. Also, after slitting, the assembly 300 may be removed via its slotted configuration from about the implanted lead or other surgical device 5 without disrupting the placement of the device 5.

Prior to opening the valve 25, the assembly 300 is in a disengaged or non-bypass state and, as a result, the valve 25 is in a closed state, as shown in FIGS. 11A-11C and 14A-14C. The bypass assembly 302 is matingly coupled to the hub 15 via the tabs 82 and tab openings 80. The hub receiving groove 330 of the bypass assembly 302 also receives the hub 15 and together with the tabs 82, hinders the movement of the cap 30 relative to the hub 15. The bypass tool 302 is received in the opening 70, 315 of the cap 30 and, in some embodiments, the tab 310 of the bypass tool 302 is received in the locking groove 335, thereby hindering longitudinal movement of the bypass tool 302 relative to the cap 30 and the valve 25. In some embodiments, as shown in FIGS. 14A-14C, the edge receiving lip 360 of the valve bypass tool 305 engages the edge 320 of the cap 30, thereby preventing the bypass tool 305 from proximally displacing off of the cap 30. Further, as shown in FIGS. 11A-11C and 14A-14C, in the disengaged state, the distal end 351 of the bypass tool 305 may abut the valve 25, but does not open the valve 25.

To open the valve 25, the assembly 300 is placed into an engaged or bypass state, wherein the bypass tool 305 is used to force the valve open 25, as shown in FIGS. 12A-12C and 15A-15C. As can be understood from FIGS. 12A-12C, in some embodiments, the tab 310 on the valve bypass tool 305 may need to be disengaged from a locking groove 335 and aligned into the channel 332 before the tool 305 can be moved distally relative to the cap 30. Once this is accomplished, the distal end 351 of the tool 305 is then free to engage the valve 25. Specifically, the tab 310 slides down the channel 332 as the tool 305 is distally displace relative to the cap 30 such that the shaft 500 is pushed through the valve 25 and the inner valve component 90, thereby placing the valve 25 in an open state. The force and friction exerted on the shaft 500 of the tool 305 via the parts of the shaft 500 through which the tool 305 extends maintains tool 305 in place within the valve 25, maintaining the valve 25 in an open state until the tool 305 is purposely proximally displaced out of the valve 25. When the tool 305 is fully extended into the valve 25, the cap side 356 of the proximal face 340 of the bypass tool 305 abuts the cap 30 and/or the tab 310 may abut the valve 25. When in an open state via the bypass tool 305, the valve 25 may receive the lead or other cardiac surgical device 5 or other secondary surgical tools. The valve 25 may be allowed to close by proximally displacing the tool 305 out of the valve 25, the tab 310 sliding proximally along the channel 332. Once fully proximally displaced out of the valve and into the disengaged state, the tab 310 may be engaged with the locking groove 335, thereby securing the tool 305 in the disengaged state. A lead or other device 5 still extending through closed valve 25 may have a hemostatic seal created about the lead or device 5 via the valve 25 being closed about the lead or device.

As can be understood from FIGS. 15A-15C, the tool 305 may be pushed distally through the valve 25 and the inner valve component 90, thereby placing the valve 25 in an open state. As already described, the forces and friction of the valve 25 acting against the tool shaft 500 extending therethrough maintains the tool 305 in place within the valve 25. When the tool 305 is fully distally displaced, the cap side 356 of the proximal face 340 of the bypass tool 305 may abut the cap 30, the wall 355 of the bypass tool 302 may slide over the outer circumference 333 of the cap 30 and the edge 320 aligns approximately with the tabs 82. In such a bypass state, the valve 25 may receive the lead or other cardiac surgical device 5 or other secondary surgical tools. The valve 25 may be closed by proximally displacing the tool 305 so as to remove the shaft 500 of the bypass tool 305 from the valve 25, the tool 305 being fully proximally displaced when the edge receiving lip 360 of the valve bypass tool 305 abuts the edge 320 of the cap 30, the assembly 300 being returned to a disengaged state.

As discussed above with respect to the delivery device 10, and as can be understood from FIGS. 9-15C, and with reference to FIG. 1, the delivery device assembly 300 is generally configured to receive a lead or other cardiac surgical device 5 at the proximal end 380 of the assembly 300, and the lead or other surgical device 5 may be guided through the lumen of the shaft 20 to the implant or desired location in the heart 35. Once the lead is implanted at the desired electrotherapy implant location or the surgical device is placed at the desired location, the delivery device 10 may be slit with a slitter 45 or other cutting tool and withdrawn from about the surgical device 5. Due to the slotted configurations of the cap 30 and tool 305, the cap and tool may be easily removed from about the surgical device 5 without disrupting the device 5.

Figure 16:
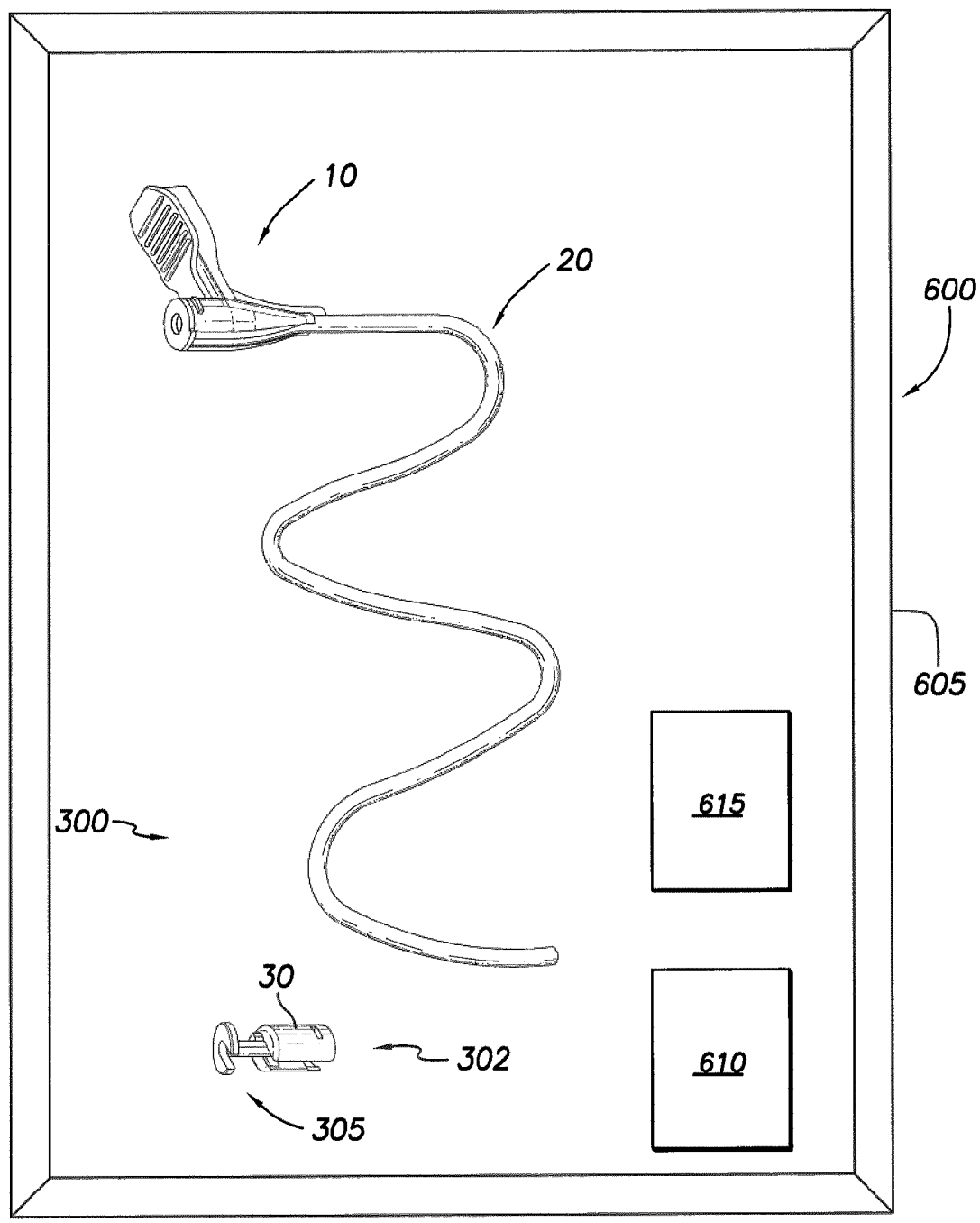
FIG. 16 is a kit comprising the slittable delivery device assembly of FIG. 9.

As can be understood from FIG. 16, the delivery device assembly 300 may be a component of a kit 600. The kit 600 may include packaging 605, the delivery device assembly 300, including the delivery device 10 and the bypass assembly 302, labeling 610 and instructions 615.

The packaging 605 may be made of plastic or other appropriate material such that some or all of the components of the kit 600 may be visible to a consumer during display. The labeling 610 may be located within the packaging 605 or on the outside of the packaging 605 and may include a listing of the components of the kit 600 and an identification of the manufacturer of the kit 600, e.g. St. Jude Medical. The instructions 615 may include a list of the components and directions for their use during a surgical procedure.

As discussed above with respect to FIG. 17, the valve bypass tool 305 may not be part of an integrated bypass assembly 302 as discussed with respect to FIGS. 9-15C, but is instead an independent and separate tool that may be used as needed with the slittable delivery device 10. In such an embodiment, the independent bypass tool 305 may not be equipped with the tab 310, but may have a shaft 500 configured to allow the separate valve bypass tool 305 to be inserted into the hemostasis valve as needed and reused as necessary during the lead implantation procedure.

In some embodiments, as discussed with respect to FIGS. 9-15C, the cap 30 and valve bypass tool 305 may form an integrated bypass assembly 302 and the assembly 302 may form with the slittable delivery device 10 an integrated assembly 300. As indicated in FIG. 16, such an embodiment may be packaged in a kit 600 where the bypass assembly 302 is provided separate from, but capable of being coupled to, the slittable delivery device 10.

In some embodiments, as discussed with respect to FIG. 17, the cap 30 may be part of the slittable delivery device 10, and the valve bypass tool 305 may be an independent tool 305 useable with the slittable delivery device 10. As indicated in FIG. 18, such a slittable delivery device 10 and independent valve bypass tool 305 may be packaged in a kit 600 similar to that discussed with respect to FIG. 16.

Any of the valve bypass assemblies 302 discussed herein with respect to FIGS. 9-15C may be employed with a slittable delivery device 10 as disclosed herein with respect to FIGS. 2-8B or with any other delivery device, including those already known in the art. Also, the independent valve bypass tool 305 discussed herein with respect to FIG. 17 may be employed with a slittable delivery device 10 as disclosed herein with respect to FIGS. 2-8B or with any other delivery device, including those already known in the art.

Although the present invention has been described with reference to preferred embodiments, persons skilled in the art will recognize that changes may be made in form and detail without departing from the spirit and scope of the invention.

What is claimed is:

1. An assembly for the delivery of a cardiac surgical device, the assembly comprising:
a slittable delivery device having a hub, a shaft integrated into the hub and forming at least a segment of the circumferential surface of the hub, and a hemostasis valve contained substantially within the hub;
wherein the shaft is formed of at least a first material;
wherein the hub has a first wall segment and a second wall segment, wherein the first wall segment comprises at least the first material and the second wall segment comprises at least a second material that is harder that the first material; and
wherein the first and second wall segments extend from a distal end of the hub to a proximal end of the hub; and
a bypass assembly having a cap and a valve bypass tool, wherein the cap is on the proximal end of the hub and has an opening in the cap extending radially outward from a point near a radial center of the cap through a circumferential edge of the cap, wherein the valve bypass tool is operably coupled to the cap and includes a longitudinally extending open channel.

2. The assembly of claim 1, wherein the cap assembly at least partially encloses the valve within the hub.

3. The assembly of claim 1, wherein the opening of the cap and the longitudinally extending open channel of the bypass tool are generally aligned.

4. The assembly of claim 1, wherein the delivery device is at least one of a catheter or sheath.

5. The assembly of claim 1, wherein the cardiac surgical device is at least one of an implantable cardiac electrotherapy lead, an inner catheter, an outer sheath, a stylet, a guidewire and a sensor.

6. A slittable delivery device for the delivery of a cardiac surgical device, the delivery device comprising:
a shaft formed of at least a first material;
a hub coupled to the shaft and including a wall including a first wall segment and a second wall segment, wherein the first wall segment includes at least the first material and the second wall segment includes at least a second material that is at least one of harder and more rigid than the first material or softer and less rigid than the first material;
a valve bypass assembly operably coupled to a proximal end of the hub; and
a hemostasis valve contained substantially within the hub;
wherein the valve bypass assembly includes a cap on a proximal end of the hub, the cap including an opening in the cap extending radially outward from a point near a radial center of the cap through a circumferential edge of the cap.

7. The delivery device of claim 6, wherein the first and second wall segments extend from a distal end of the hub to a proximal end of the hub.

8. The delivery device of claim 6, wherein the second wall segment forms a substantially greater percentage of the wall surface than the first wall segment.

9. The delivery device of claim 6, wherein the device is at least one of a catheter or sheath.

10. The delivery device of claim 6, wherein the first and second wall segments are longitudinally extending wall segments.

11. The delivery device of claim 6, further comprising a valve bypass tool including a longitudinally extending slot at least partially aligned with the opening in the cap.

12. The delivery device of claim 6, wherein the cardiac surgical device is at least one of an implantable cardiac electrotherapy lead, an inner catheter, an outer sheath, a stylet, a guidewire and a sensor.

13. A slittable delivery device for the delivery of a cardiac surgical device, the delivery device comprising:
a slittable shaft;
a slittable hub having a proximal end and a distal end, the slittable hub coupled to a proximal end of the slittable shaft;
a consistent slitting medium extending generally the longitudinal lengths of the shaft and hub;
wherein the proximal end of the slittable shaft longitudinally splits into an exposed portion, wherein the exposed portion extends from the distal end of the slittable hub to the proximal end of the slittable hub to form a segment of a circumferential surface of the slittable hub, and wherein a slit is formed through the exposed portion upon removal of the slittable delivery device;
a hemostasis valve coupled to the hub; and
a valve bypass tool extendable into the hemostasis valve.

14. The delivery device of claim 13, wherein the consistent slitting medium includes a material of the shaft.

15. The delivery device of claim 13, wherein the delivery device is at least one of a catheter or sheath.

16. The delivery device of claim 13, wherein the cardiac surgical device is at least one of an implantable cardiac electrotherapy lead, an inner catheter, an outer sheath, a stylet, a guidewire and a sensor.

17. The delivery device of claim 13, wherein the valve bypass tool includes a longitudinally extending slot configured to allow the removal of the cardiac surgical device without having to cut the valve bypass tool.

18. The delivery device of claim 17, further comprising a slotted cap that maintains the hemostasis valve coupled to the hub, wherein the slotted cap is configured to allow the removal of the slotted cap without having to cut the slotted cap.

19. A medical kit for the delivery of at least one of an implantable cardiac electrotherapy lead, an inner catheter, an outer sheath, a stylet, a guidewire and a sensor, the medical kit comprising:
a slittable delivery device having a slittable shaft, a slittable hub coupled to a proximal end of the slittable shaft, and a consistent slitting medium extending generally the longitudinal lengths of the slittable shaft and slittable hub;

wherein the slittable shaft is formed of at least a first material;

wherein the slittable hub comprises a first wall segment and a second wall segment, wherein the first wall segment includes at least the first material and the second wall segment includes at least a second material that is harder that the first material; and wherein the first and second wall segments extend from a distal end of the hub to a proximal end of the hub;

a valve bypass tool including a longitudinally extending channel; and a package enclosing the slittable delivery device and the valve bypass tool.

20. The medical kit of claim 19, further comprising instructions indicating the slittable delivery device is to be slit along the consistent slitting medium.

21. The medical kit of claim 19, further comprising instructions indicating the longitudinally extending channel is to be used to remove from within the valve bypass tool the at least one of an implantable cardiac electrotherapy lead, an inner catheter, an outer sheath, a stylet, a guidewire and a sensor.

22. The medical kit of claim 19, further comprising instructions indicating the valve bypass tool is displaceable through a hemostasis valve coupled to the hub.

23. A medical kit for the delivery of at least one of an implantable cardiac electrotherapy lead, an inner catheter, an outer sheath, a stylet, a guidewire and a sensor, the medical kit comprising:

a slittable delivery device having a shaft, a hub coupled to a proximal end of the shaft, and a consistent slitting medium extending generally the lengths of the shaft and hub;

wherein a proximal end of the shaft longitudinally splits into an exposed portion, wherein the exposed portion extends from a distal end of the hub to a proximal end of the hub to form a segment of a circumferential surface of the hub, and wherein a slit is formed through the exposed portion upon removal;

a hemostasis valve coupled to the hub; and a package enclosing the slittable delivery device and the valve bypass tool.

24. The medical kit of claim 23, further comprising instructions indicating the slittable delivery device is to be slit along the consistent slitting medium.

* * * * *